US009862947B2

(12) United States Patent
Cheng et al.

(10) Patent No.: US 9,862,947 B2
(45) Date of Patent: *Jan. 9, 2018

(54) SELECTIVE REDUCTION OF THE DELETERIOUS ACTIVITY OF EXTENDED TRI-NUCLEOTIDE REPEAT CONTAINING GENES

(71) Applicants: The Board of Trustees of the Leland Stanford Junior University, Stanford, CA (US); National Yang-Ming University, Taipei (TW)

(72) Inventors: Tzu-Hao Cheng, Taipei (TW); Chia-Rung Liu, Tainan (TW); Tzu-Han Wang, Taipei (TW); Stanley N. Cohen, Stanford, CA (US)

(73) Assignees: The Board of Trustees of the Leland Stanford Junior University, Stanford, CA (US); National Yang-Ming University, Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 14/961,689

(22) Filed: Dec. 7, 2015

(65) Prior Publication Data

US 2016/0152978 A1   Jun. 2, 2016

Related U.S. Application Data

(63) Continuation of application No. 13/988,605, filed as application No. PCT/US2011/063997 on Dec. 8, 2011, now Pat. No. 9,211,303, and a continuation-in-part of application No. 13/110,494, filed on May 18, 2011, now Pat. No. 8,569,254.

(60) Provisional application No. 61/513,970, filed on Aug. 1, 2011.

(30) Foreign Application Priority Data

Dec. 10, 2010 (TW) .............................. 099143336 A

(51) Int. Cl.
| | |
|---|---|
| C07H 21/02 | (2006.01) |
| C07H 21/04 | (2006.01) |
| C12Q 1/68 | (2006.01) |
| C12N 15/113 | (2010.01) |
| A61K 31/713 | (2006.01) |
| G01N 33/50 | (2006.01) |
| C12N 5/00 | (2006.01) |
| A61K 51/10 | (2006.01) |

(52) U.S. Cl.
CPC .......... *C12N 15/113* (2013.01); *A61K 31/713* (2013.01); *C12Q 1/6876* (2013.01); *G01N 33/5023* (2013.01); *A61K 51/10* (2013.01); *A61K 51/1075* (2013.01); *C12N 2310/14* (2013.01); *C12N 2320/30* (2013.01); *C12Q 2600/136* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 8,569,254 B2 | 10/2013 | Cheng et al. | |
| 9,211,303 B2 * | 12/2015 | Cheng | .................. A61K 31/713 |
| 9,226,935 B2 * | 1/2016 | Cheng | |
| 2005/0020521 A1 | 1/2005 | Rana | |
| 2005/0096284 A1 * | 5/2005 | McSwiggen | ..... A61K 47/48053 514/44 R |
| 2006/0270623 A1 | 11/2006 | McSwiggen | |
| 2007/0105803 A1 * | 5/2007 | Manoharan | ........... C12N 15/111 514/44 A |
| 2007/0174924 A1 | 7/2007 | Allen | |
| 2008/0070246 A1 | 3/2008 | Cheng et al. | |

(Continued)

FOREIGN PATENT DOCUMENTS

| | | |
|---|---|---|
| WO | WO 2004/041838 A1 | 5/2004 |
| WO | WO 2005/027980 A1 | 3/2005 |

(Continued)

OTHER PUBLICATIONS

Apostol et al. "A cell-based assay for aggregation inhibitors as therapeutics of polyglutamine-repeat disease and validation in *Drosophila*", Proc. Natl. Acad. Sci. USA. (May 2003), 100(10):5950-5.

Cummings et al. "Fourteen and counting: unraveling trinucleotide repeat diseases", Human Molecular Genetics (Apr. 2000), 9(6):909-916.

Difiglia et al. "Therapeutic silencing of mutant huntingtin with siRNA attenuates striatal and cortical neuropathology and behavioral deficits", Proc. Natl. Acad. Sci. USA. (Oct. 2007), 104(43):17204-9.

Furling et al. "Viral vector producing antisense RNA restores myotonic dystrophy myoblast functions", Gene Ther. (May 2003), 10(9):795-802.

(Continued)

*Primary Examiner* — Sean McGarry
(74) *Attorney, Agent, or Firm* — Glenn J. Foulds; Bret E. Field; Bozicevic, Field & Francis LLP

(57) ABSTRACT

Aspects of the invention include methods of selectively reducing the deleterious activity of mutant extended trinucleotide repeat containing genes in a cell, as well as compositions used in such methods. The deleterious activity (e.g., toxicity and/or dis-functionality of products encoded thereby) of a mutant extended trinucleotide repeat containing gene may be selectively reduced in a variety of different ways, e.g., by selectively decreasing SPT4 mediated transcriptional activity, by enhancing functionality of proteins encoded thereby, etc. Aspects of the invention further include assays for identifying agents that find use in methods of the invention, e.g. as summarized above. Methods and compositions of the invention find use in a variety of different applications, including the prevention or treatment of disease conditions associated with the presence of genes containing mutant extended trinucleotide repeats, such as Huntington's Disease (HD).

20 Claims, 11 Drawing Sheets

(56) References Cited

U.S. PATENT DOCUMENTS

| | | | |
|---|---|---|---|
| 2008/0176812 A1 | 7/2008 | Davidson et al. | |
| 2008/0318884 A1 | 12/2008 | Detloff et al. | |
| 2011/0172291 A1 | 7/2011 | Aronin et al. | |
| 2013/0059902 A1* | 3/2013 | Corey | C12N 15/113 514/44 A |
| 2015/0159155 A1* | 6/2015 | Hung | C12N 15/113 514/44 A |

FOREIGN PATENT DOCUMENTS

| | | |
|---|---|---|
| WO | WO 2011/016840 | 2/2011 |
| WO | WO 2012/078906 | 6/2012 |

OTHER PUBLICATIONS

Gorbunova et al. "Genome-wide demethylation destabilizes CTG. CAG trinucleotide repeats in mammalian cells", Human Molecular Genetics (Dec. 2004), 13(23):2979-2989.

Helene et al. "Specific regulation of gene expression by antisense, sense and antigene nucleic acids", Biochimica et Biophysica Acta, vol. 1049 (1990), pp. 99-125.

Hu et al. "Allele-specific silencing of mutant huntingtin and ataxin-3 genes by targeting expanded CAG repeats in mRNAs", Nat. Biotechnol. (May 2009), 27(5):478-84.

Liu et al. "Spt4 is selectively required for transcription of extended trinucleotide repeats", Cell (Feb. 2012), 148(4):690-701.

Omi et al. "14-3-3zeta is indispensable for aggregate formation of polyglutamine-expanded huntingtin protein", Neurosci Lett. (Jan. 2008), 431(1):45-50.

Sánchez et al. "Pivotal role of oligomerization in expanded polyglutamine neurodegenerative disorders", Nature (Jan. 2003), 421(6921):373-9.

Wang et al. "Clinico-pathological rescue of a model mouse of Huntington's disease by siRNA", Neurosci Res. (Nov. 2005), 53(3):241-9.

Chen et al. "DSIF, the Paf1 complex, and Tat-SF1 have nonredundant, cooperative roles in RNA polymerase II elongation", Genes & Development (2009) 23: 2765-2777.

Liu et al. "Spt4 Is Selectively Required for Transcription of Extended Trinucleotide Repeats", Cell (Feb. 2012) 148:690-701.

Sims et al. "Elongation by RNA polymerase II: the short and long of it", Genes & Development (2004) 18:2437-2468.

Wu et al. "NELF and DSIF cause promoter proximal pausing on the hsp70 promoter in *Drosophila*", Genes & Development (2003) 17:1402-1414.

\* cited by examiner

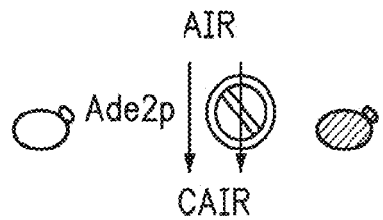
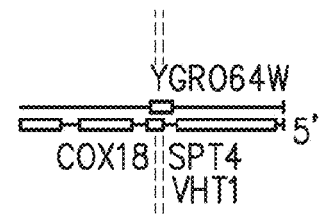
FIG. 1A
FIG. 1E
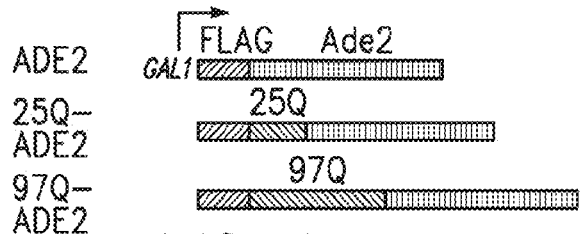
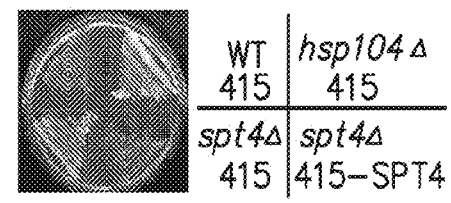
FIG. 1B
FIG. 1F
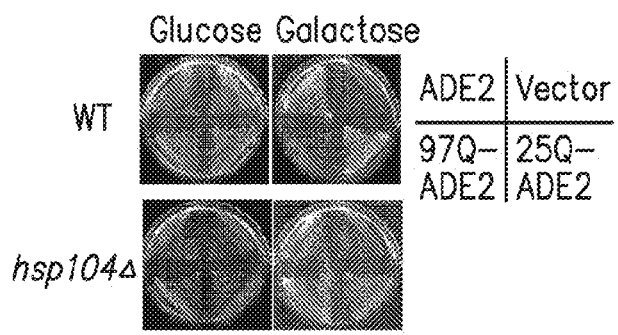
FIG. 1C
FIG. 1G
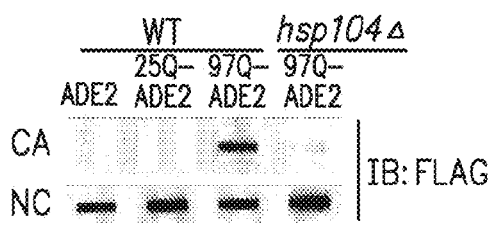
FIG. 1D

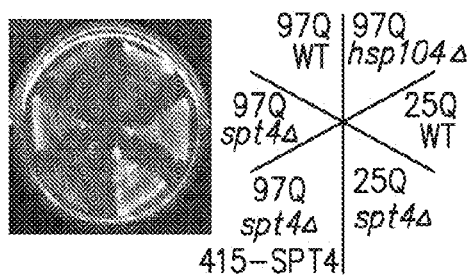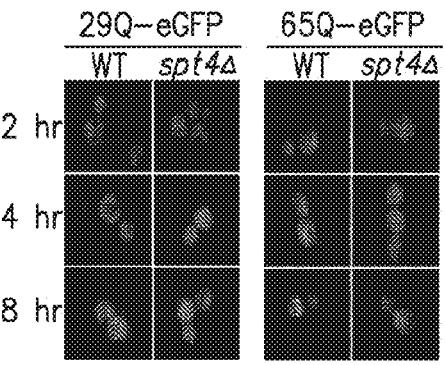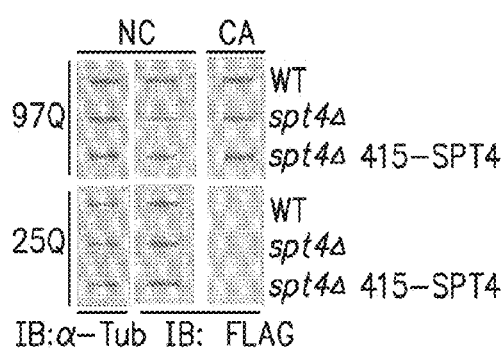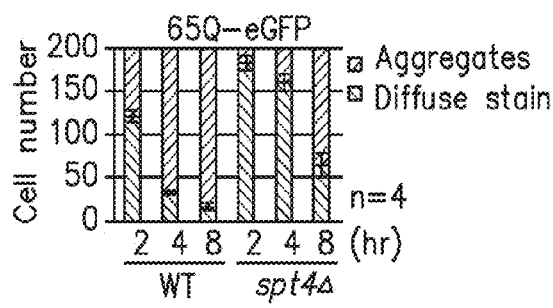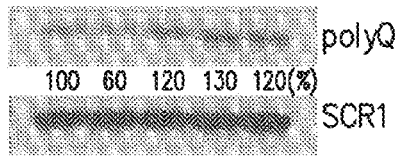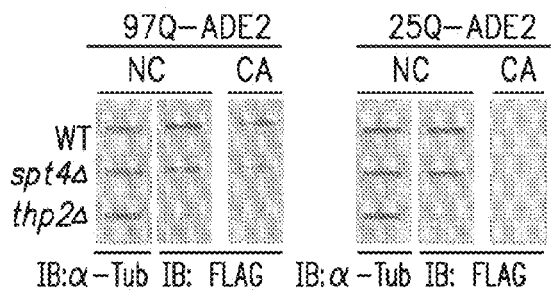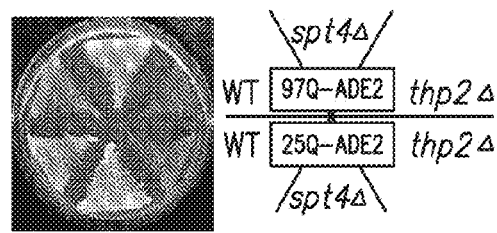
FIG. 2A
FIG. 2B
FIG. 2C
FIG. 2D
FIG. 2E
FIG. 2F

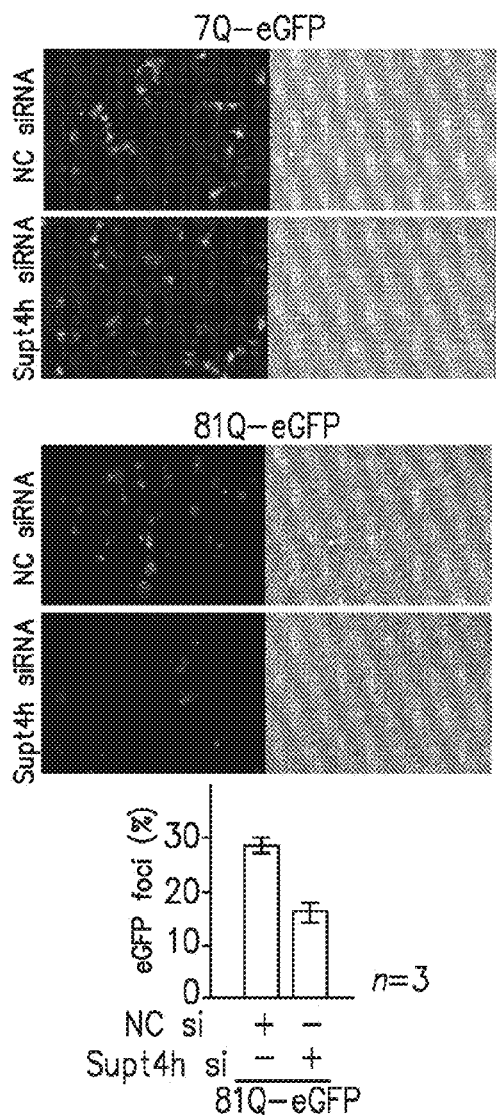
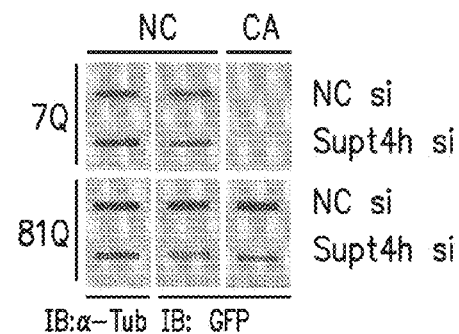
FIG. 5C
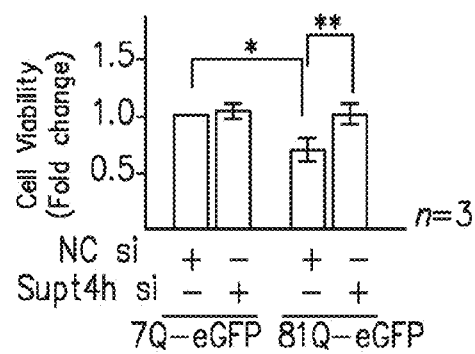
FIG. 5D
FIG. 5A
FIG. 5B

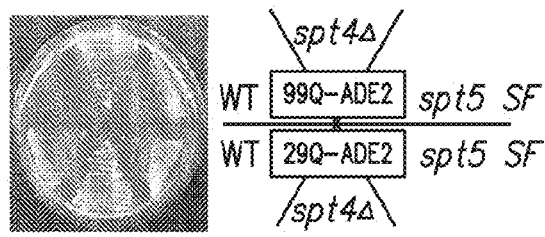
FIG. 11A
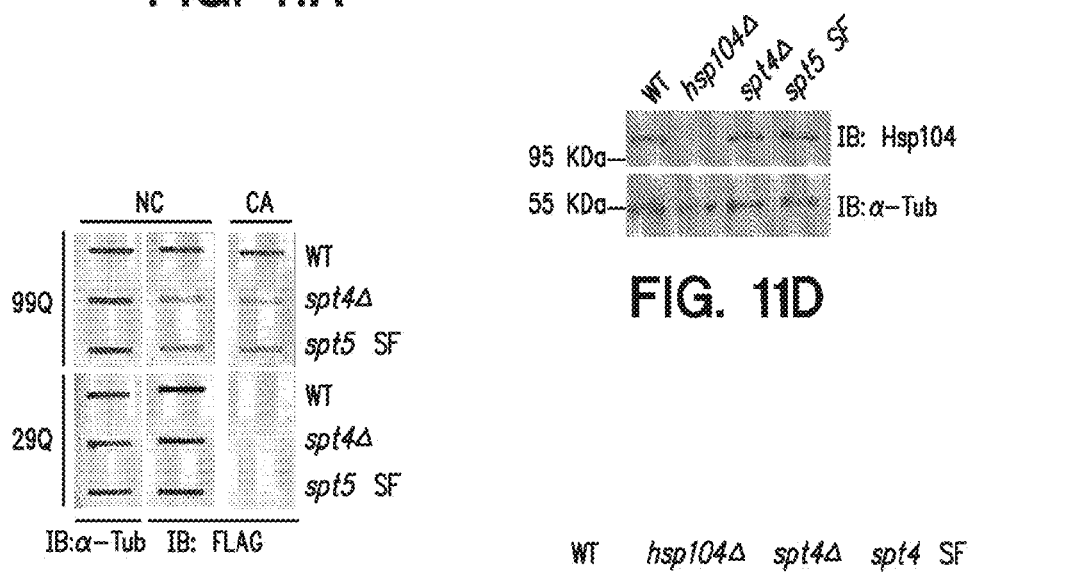
FIG. 11D
FIG. 11B
FIG. 11E
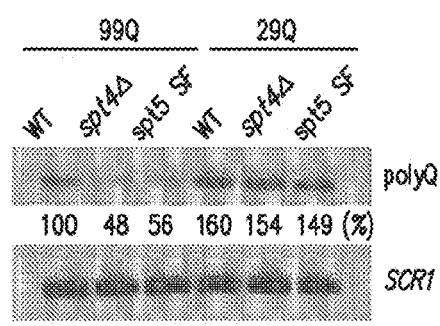
FIG. 11C

SELECTIVE REDUCTION OF THE DELETERIOUS ACTIVITY OF EXTENDED TRI-NUCLEOTIDE REPEAT CONTAINING GENES

CROSS-REFERENCE TO RELATED APPLICATIONS

This application is a continuation application of U.S. patent application Ser. No. 13/988,605 filed on Aug. 5, 2013 and issued as U.S. Pat. No. 9,211,303 on Dec. 15, 2015, which application is a 371 International of PCT/US2011/063997 filed on Dec. 8, 2011, which application, pursuant to 35 U.S.C. §119 (e), claims priority to the filing date of U.S. Provisional Patent Application Ser. No. 61/513,970 filed on Aug. 1, 2011; the disclosures of which applications are herein incorporated by reference. International Application Serial No. PCT/US2011/063997 filed on Dec. 8, 2011 is also a continuation-in-part application of U.S. application Ser. No. 13/110,494 filed on May 18, 2011 and issued as U.S. Pat. No. 8,569,254; which application claims priority to Taiwanese Patent Application No. 099143336 filed on Dec. 10, 2010; the disclosures of which applications are herein incorporated by reference.

GOVERNMENT RIGHTS

This invention was made with Government support under contract RR025744 awarded by the National Institutes of Health. The Government has certain rights in the invention.

BACKGROUND

Polyglutamine (PolyQ) diseases are a class of diseases consisting of nine genetically distinct disorders. They include Huntington's disease (HD), dentatorubral-pallidoluysian astrophy (DRPLA), SBMA and spino-cerebellar ataxia 1, 2, 3, 6, 7 and 17 (SCA1/2/3/6/7/17). Because these diseases are caused by the expansion of a translated CAG repeats that codes for the glutamines, they are also known as CAG repeat diseases.

One common physiological characteristic shared among these genetically distinct diseases is that patients who suffer from the diseases are all found to have proteinaceous deposits in their brains. Although in each of these diseases, the proteinaceous deposit is associated with a different protein, the proteins all contain an expanded stretch of glutamines. To date, this expanded stretch of polyQ sequence in the disease-related proteins is the only known genetic mutation implicated in all the polyQ diseases.

Additional tri-nucleotide repeat diseases exist in which expansion of the repeat is located within regions of the gene that do not encode a protein. Examples of such repeats include CAG or CTG tri-nucleotide repeats. RNA encoded by genes that contain such repeats may form foci that incorrectly localize or regulate RNA binding proteins, leading to detrimental effects.

Among polyQ diseases, HD is perhaps the most well-known among the general public because of its devastating effects on the patients. The disease is associated with selective neuronal cell death occurring primarily in the cortex and striatum. It is a fatal and cruel disease that progressively deprives patients of their movement, cognition, and personality, exacting significant economic and emotional tolls on the patients and their families. The frequency of HD is particularly prevalent among people of Western European descent (about 1 in 20,000). Unfortunately, there is presently no cure for this terrible disease.

Currently, available treatments for HD are mainly limited to managing the macroscopic symptoms. For example, one of the newest compounds approved by the FDA, tetrabenazine, is a drug for reducing hyperkinetic movements in HD patients. Tetrabenazine is a vesicular monoamine transporter (VMAT) inhibitor which promotes early degradation of neurotransmitters. Thus, the drug merely treats the symptom, not the root of the disease. Other drugs currently used for treating HD include neuroleptics and benzodiazepines. No presently known treatment is attempting to address the root cause of HD.

As mentioned above, the root cause of HD is an abnormal expansion of CAG repeats in a gene within the CNS cells, specifically the gene Htt which encodes the protein huntingtin (Htt). In a normal person, there are about 8-25 constitutive repeats of CAG nucleotide sequence in the Htt gene. In a HD patient, the number of CAG repeats are expanded to 36 or more. Because this type of mutation is dominant, a person only needs to inherit one copy of the mutated huntingtin gene to develop HD.

Recent cell and animal model studies have provided evidence that aggregates formed by mutant Htt play a critical role in the progression of HD. It has been observed that the mutant Htt proteins can leave behind shorter fragments from parts of the polyQ expansion when subjected to proteolytic cleavages. If too many copies of glutamine exist in the mutant Htt, the polar nature of glutamine will lead to undesirable interactions with other proteins. In particular, mutant Htt with too many copies of glutamines will form hydrogen bonds with one another and aggregate rather than fold into functional proteins. Over time, the accumulated protein aggregates will damage the neuronal cells, leading to cell death and neurological deficit in the patient. The damaging effects of the protein aggregates have been corroborated by experiments showing that chemical reagents capable of inhibiting the formation of protein aggregates can enhance survival of cells and ameliorate pathology of HD in a mouse model. However, notwithstanding such evidence, it has been argued by some scientists that visible aggregates represent a coping response that cells use to sequester toxic proteins containing extended polyQ regions.

SUMMARY

Aspects of the invention include methods of selectively reducing the deleterious activity of mutant extended tri-nucleotide repeat containing genes in a cell, as well as compositions used in such methods. The deleterious activity (e.g., toxicity and/or dis-functionality of products encoded thereby) of a mutant extended trinucleotide repeat containing gene may be selectively reduced in a variety of different ways, e.g., by selectively decreasing SPT4 mediated transcriptional activity, by enhancing functionality of proteins encoded thereby, etc. Aspects of the invention further include assays for identifying agents that find use in methods of the invention, e.g. as summarized above. Methods and compositions of the invention find use in a variety of different applications, including the prevention or treatment of disease conditions associated with the presence of genes containing mutant extended trinucleotide repeats, such as Huntington's Disease (HD).

BRIEF DESCRIPTION OF THE FIGURES

The file of this patent contains at least one drawing executed in color. Copies of this patent with color drawing(s) will be provided by the Patent and Trademark Office upon request and payment of the necessary fee.

FIG. 1A-1G. SPT4 mutation confers decreased 97Q-Ade2 aggregation (FIG. 1A) Principle of colony color assay. Deficiency of Ade2 leads to AIR accumulation and confers a color change from white to red. (FIG. 1B) Diagram of plasmid constructs expressing Ade2, 25Q-Ade2, and 97Q-Ade2. Fusion proteins contain an N-terminal FLAG epitope and are expressed under control of the GAL1 promoter. (FIG. 1C) Colony color phenotypes of cells expressing indicated constructs. Both wild-type (W303-1A) and isogenic hsp104Δ cells possess the ade2-1 mutant allele and are red in glucose media. (FIG. 1D) Results of filter-trap assay to detect polyQ-Ade2 aggregates. Lysates were collected from cells as shown in (FIG. 1C) and loaded onto a cellulose acetate (CA) membrane, which traps only aggregated protein. Retention of polyQ-Ade2 on the membrane is detected by immunoblot using anti-FLAG antibody. A slot blot assay using nitrocellulose (NC) membranes was included as a loading control. (FIG. 1E) Diagram showing transposon module insertion site in the clone 23-44. (FIG. 1F) Colony color phenotypes of cells expressing 97Q-Ade2 in the absence and presence Spt4. 97Q-ADE2 plasmid together with empty vector 415 or the Spt4 expression construct 415-SPT4 were transformed into indicated cells. Spt4Δ and hsp104Δ were derived from wild-type (WT) cells by deleting the entire open reading frame of corresponding genes. Cells were grown on medium with galactose as the sole carbon source. (FIG. 1G) Analysis of 97Q-Ade2 aggregation in spt4 mutant cells. Comparable protein extracts from cells as described in (FIG. 1F) were loaded onto CA membranes and immunoblotted with anti-FLAG antibody. α-Tubulin (α-Tub) was examined by slot blot assay (NC membrane) and served as a loading control. See also FIG. 8A-8C.

FIG. 2A-2F. Spt4 selectively regulates expression and aggregation of proteins containing expanded polyQ repeats (FIG. 2A) Colony color phenotypes of cells expressing 97Q-Ade2 or 25Q-Ade2. (FIG. 2B) Analysis of cellular 97Q- and 25Q-Ade2 protein expression and aggregation. A NC membrane from the slot blot was immunoblotted with anti-FLAG antibody to determine polyQ-Ade2 protein levels. α-Tubulin (α-Tub) served as loading control. Aggregation of polyQ-Ade2 was assessed by a filter-trap assay (CA membrane). (FIG. 2C) Expression of mRNA encoding 97Q- or 25Q-Ade2 was examined by Northern blot. mRNAs were detected by a probe that recognizes the polyQ coding sequence. After normalization with SCR1, the mRNA abundance was set as 100% in WT cells expressing 97Q-ADE2. By comparison, relative mRNA abundance in each indicated cell type is shown. (FIG. 2D) Upper panels, analysis of polyQ-mediated eGFP aggregation in wild-type and spt4Δ cells. Cells harboring the 29Q- or 65Q-eGFP plasmid construct were examined by fluorescence microscopy after gene induction at 2, 4, and 8 hr. At each time point, 200 cells were examined and the appearance of foci was defined as an indicator of eGFP aggregation. Cells lacking foci are defined as showing "Diffuse stain". Lower panel, the number of cells having 65Q-eGFP aggregates is illustrated as a function of time. Data is the average of four independent experiments, and the bar represents standard deviation. (FIG. 2E) 97Q-Ade2 and 25Q-Ade2 protein expression in thp2Δ cells was analyzed by a slot blot assay (NC). A filter-trap assay (CA) was also employed. THP2 encodes a subunit of the THO complex. (FIG. 2F) Colony color phenotypes of thp2Δ cells expressing either 97- or 25Q-Ade2. See also FIG. 9A-9C, FIG. 10A-10C, and FIG. 11A-11E.

(FIG. 4B) Expression and aggregation of polyQ-Ade2 were assessed by slot blot (NC) and filter-trap (CA) assay, respectively. Anti-FLAG antibody was used to probe 29Q-Ade2-HA, 29Q-Ade2, and 99Q-Ade2, while anti-HA antibody detected only 29Q-Ade2-HA. (FIG. 4C) Expression of transcripts encoding polyQ-Ade2 proteins was examined by Northern blotting. The positions of 99Q-ADE2 and 29Q-ADE2-HA are indicated by arrows.

FIG. 5A-5D. Supt4h regulates expression, aggregation, and toxicity of 81Q-eGFP in striatal neural cells (FIG. 5A) Left, murine ST14A striatal cells transfected with the 7Q-eGFP or 81Q-eGFP plasmid construct together with control (NC si) or Supt4h siRNA (Supt4h si) were monitored by fluorescence microscopy. Right, phase contrast images are shown. Lower panel, percentage of cells showing 81Q-eGFP foci under these conditions. The values shown are the means±SD for three independent experiments. (FIG. 5B) Changes in Supt4h expression upon siRNA knockdown were analyzed by Western blot. To ensure comparable transfection efficiency among samples, pRC-CMV-MnSOD was co-transfected and its protein expression determined. (FIG. 5C) Expression and aggregation of polyQ-eGFP were assessed by slot blot (NC) and filter-trap (CA) assay, respectively. (FIG. 5D) Viability of ST14A cells expressing 7Q-eGFP or 81Q-eGFP was measured with and without Supt4h siRNA knockdown. After transfection with indicated polyQ-eGFP and siRNA, cells were cultured in growth media containing a minimal amount (0.5%) of serum and maintained at 39° C. to induce neuronal cell differentiation. The number of viable cells expressing 7Q-eGFP in the presence of control siRNA was set as 1, and the relative cell viability of other samples is illustrated (*, **P<0.05 by Student t-test).

(FIG. 6B) Changes in mRNA expression by Supt4h siRNA knockdown were assessed by real-time qRT-PCR. Each mRNA was normalized with U6 and the transcript abundance in cells transfected with control siRNA was set as 1. (FIG. 6C) Analysis of protein expression in cells in presence or absence of Supt4h siRNA transfection. Equal amounts of total protein extracts were immunoblotted for Htt, Supt4h, Tbp, and α-Tubulin. Tbp, the TATA box binding protein, was included as a representative of short CAG repeat-containing genes. (FIG. 6D) Striatal cells with heterozygous Htt alleles (Hdh$^{Q7/Q111}$) were transfected with Supt4h siRNA and protein expression was analyzed as described in (FIG. 6C). The positions of Htt$^{Q7}$ and Htt$^{Q111}$ are indicated by arrows.

(FIG. 8B) Analysis of [PIN+] status by RNQ1-GFP labeling. The RNQ1-GFP plasmid construct was introduced into cells and monitored by fluorescence microscopy. Cells with [PIN+] show GFP-positive foci, whereas the GFP signal is evenly distributed in cells lacking [PIN+]. WT and hsp104D served as positive and negative controls for [PIN+], respectively. (FIG. 8C) Hsp104 protein levels in indicated cells were examined by immunoblotting using anti-Hsp104 antibody.

(FIG. 9B) Cellular expression and aggregation of 97Q-Ade2 protein was determined by slot blot (NC) and filter-trap (CA) assay, respectively. Antibody against the FLAG-epitope was used to detect 97Q-Ade2. (FIG. 9C) Colony color phenotypes of 97Q-ADE2 expression cells in growth media as described in (FIG. 9A). WT (W303-1A) cells possess the ade2-1 mutant allele and this cell with empty vector or galactose-inducible ADE2 was included as a control.

(FIG. 10B) PolyQ-Ade2 expression and aggregation were examined using slot blot (NC) and filter-trap (CA) assays, respectively. Anti-FLAG antibody was used to detect reporter proteins. (FIG. 10C) Levels of mRNA encoding 99Q-Ade2 or 29Q-Ade2 in indicated cells were analyzed by Northern blot using a polyQ probe. After normalization with SCR1, the mRNA level of WT cells expressing 99Q-ADE2 was set as 100%. Relative mRNA levels in other cells are shown.

FIG. 11A-11E. A spt5 SF mutant specifically suppresses expression of genes with expanded CAG repeats, related to FIG. 2A-2F (FIG. 11A) Colony color phenotypes of cells expressing 99Q-Ade2 or 29Q-Ade2. Spt5 SF cells carry a specific SPT5 S324F point mutation that inhibits formation of a Spt4/5 complex (Guo, M., Xu, F., Yamada, J., Egelhofer, T., Gao, Y., Hartzog, G. A., Teng, M., and Niu, L. (2008). Core structure of the yeast spt4-spt5 complex: a conserved module for regulation of transcription elongation. Structure 16, 1649-1658). (FIG. 11B) PolyQ-Ade2 expression and aggregation were examined by slot blot (NC) and filter-trap (CA) assays, respectively. (FIG. 11C) Levels of mRNAs encoding polyQ-Ade2 were analyzed by Northern blot using a polyQ probe. After normalization with SCR1, mRNA levels in WT cells expressing 99Q-ADE2 were set at 100%. Relative mRNA levels in other cells are indicated. (FIG. 11D) and (FIG. 11E) Hsp104 protein expression and yeast prions [PIN+] were analyzed in spt5 SF cells as described in FIG. 8A-8C.

(FIG. 12B) In GM09197, there is a polymorphism in which one gag trinucleotide is deleted in the mutant Htt allele (Zhang, Y., Engelman, J., and Friedlander, R. M. (2009). Allele-specific silencing of mutant Huntington's disease gene. J Neurochem 108, 82-90.), as shown above. We designed primers spanning this region (red) to distinguish wild-type from mutant Htt. Together with a primer (5'-cgaggatctcgtcttctgaag-3') that anneals to the Htt exon 60, wild-type (WT) primer was used to amplify a 305 bp fragment by PCR using W plasmid as a template. The mutant (Mu) primer showed comparable amplification efficiency when the M plasmid was used. W and M plasmids contain sequence from exon 57 to exon 61 of GM09197 wild-type and mutant Htt mRNA, respectively. (FIG. 12C) Expression of Htt alleles in GM09197 was analyzed by RT-PCR using primers described in (FIG. 12B).

DETAILED DESCRIPTION

Figure 3:
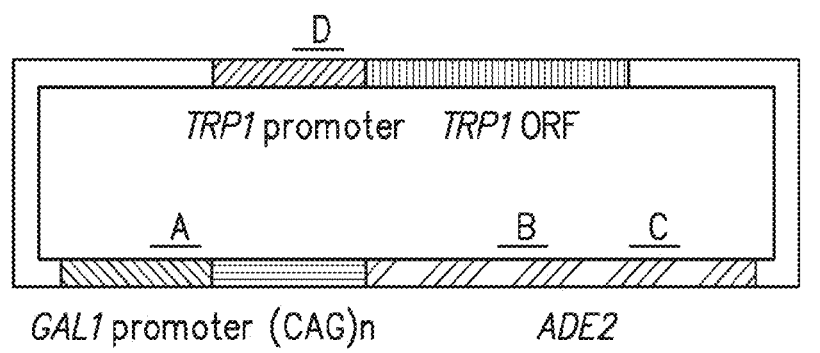
FIG. 3. Spt4 mutant cells show impaired RNA polymerase II transcription through a long stretch of CAG repeats In wild-type and spt4Δ cells, the amount of RNA polymerase II on a transcribing gene containing either 29 or 99 CAG repeats was determined by chromatin immunoprecipitation. Lower panels, precipitated DNA fragment upstream of CAG repeats was examined using primer set A, while primer sets B and C were used to detect DNA downstream of CAG repeats. Primer set D specific for the TRP1 promoter was included as control. Upper panel, the DNA region amplified by each PCR primer set is indicated in the plasmid diagram.
Figure 3:
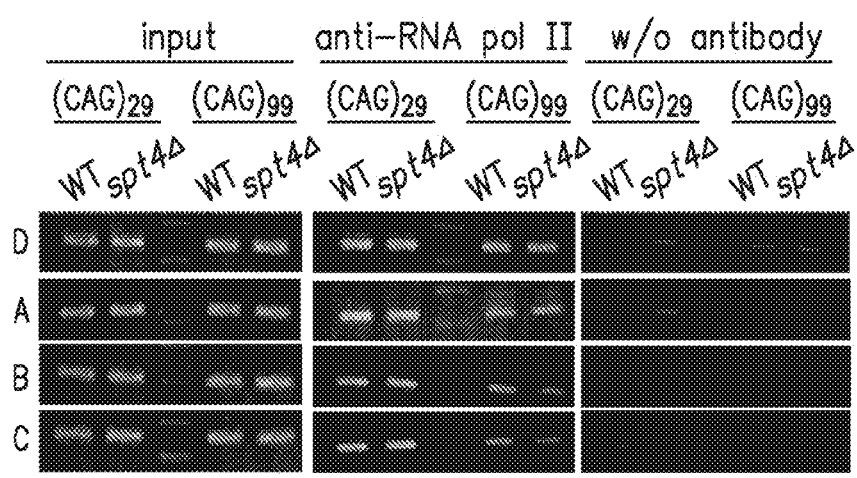

Aspects of the invention include methods of selectively reducing the deleterious activity of mutant extended trinucleotide repeat containing genes in a cell, as well as compositions used in such methods. The deleterious activity (e.g., toxicity and/or dis-functionality of products encoded thereby) of a mutant extended trinucleotide repeat containing gene may be selectively reduced in a variety of different ways, e.g., by selectively decreasing SPT4 mediated transcriptional activity, by enhancing functionality of proteins encoded thereby, etc. Aspects of the invention further include assays for identifying agents that find use in methods of the invention, e.g. as summarized above. Methods and compositions of the invention find use in a variety of different applications, including the prevention or treatment of disease conditions associated with the presence of genes containing mutant extended trinucleotide repeats, such as Huntington's Disease (HD).

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods

As summarized above, aspects of the invention include selectively reducing the deleterious impact of a gene that includes an extended trinucleotide repeat. In other words, embodiments of the invention include methods of reducing an extended trincleotide repeat containing gene's harmful or injurious activity in a cell. As these methods are methods of reducing such activity, they result in the reduction of such activity as compared to suitable control, e.g., by a statistically significant amount, and in some instances by 2-fold or more, such as 5-fold or more, including by 10-fold or more.

As the methods are methods of selectively reducing the deleterious impact, i.e., activity, of the target gene, they do so while retaining at least a statistically measurable amount of normal or wild-type, e.g., beneficial, activity of the target gene, by which is meant the activity of the gene as present in normal or wild-type cells, which are cells in which the target gene does not include mutant extended trinucleotide repeat that gives rise to deleterious activity. Accordingly, methods of the invention result in the presence of physiologically desirable activity of the target gene despite the selective reduction of the harmful activity of the target gene.

The deleterious impact or activity of the target gene that is reduced in embodiments of the invention may vary, where deleterious activities include, but are not limited to, toxicity (e.g., as a result of protein aggregation), loss of function, etc. As such, in some instances the methods result in a reduction in toxicity that is attributable to the target gene, where the magnitude of the toxicity reduction may vary, and in some instances is 2-fold or greater, such as 5-fold or greater, including 10-fold or greater, e.g., as compared to a suitable control. As described in greater detail below, toxicity may be reduced in a number of different ways which may depend on the particular target gene. In some instances, e.g., where the target gene includes an extended CAG repeat which results in the presence of extended polyQ domains in a product encoded by the target gene, toxicity reduction may be accompanied by a reduction in aggregation of the products encoded by the target gene. In such instances, the magnitude of the reduction in aggregation may vary, and in some instances the magnitude of reduction is 2-fold or more, such as 5-fold or more, including 10-fold or more. Protein aggregation may be assayed using any convenient protocol, including but not limited to the protocols described in Published United States Patent Application No. 20110130305; the disclosure of which protocols are herein incorporated by reference.

As mentioned above, the deleterious impact or activity that is reduced by methods of the invention may be loss of function of a product encoded by the target gene. In such instances, the wild-type or normal activity of the product encoded by the target gene is at least partially, if not completely, impaired because the target gene includes the extended trinucleotide repeat. In these instances, the loss of function is at least partially, if not completely, reversed by enhancing the desired function of the product of the target gene. The desired function of the encoded product may be enhanced by a statistically significant amount as compared to a suitable control, where the magnitude of the enhancement in desired activity may be 2-fold or higher, such as 5-fold or higher, including 10-fold or higher.

The target gene is a gene that includes a mutant extended trinucleotide repeat. The term "gene" as used herein is a defined region or portion of a chromosome that encodes or enables production of a product and includes a promoter, introns, exons and enhancers. By mutant extended trinucleotide repeat is meant a domain (i.e., region) of the gene that includes multiple adjacent repeats of the same three nucleotides, where the length and particular sequence of the mutant extended trinucleotide repeat may vary and the mutant extended trinucleotide repeat domain is not present in normal versions of the gene. The extended trinucleotide repeat domain may be present in a coding or non-coding region of the target gene. In embodiments, the mutant repeat domain is present in a non-coding region of the target gene, such as the CTG expansion located in the 3' untranslated region of the dystrophia myotonica-protein kinase gene, which leads to Myotonic dystrophy (DM). In some instances, the mutant repeat domain is present in a coding region of the target gene, such that in some instances its presence in the target gene results in a corresponding domain or region (e.g., polyQ domain) in a product encoded by the gene.

The mutant extended trinucleotide repeat may vary in terms of nucleotide composition and length. Specific trinucleotides of interest include, but are not limited to: CAG, CTG, and the like. In some instances, the extended trinucleotide repeat domain is a CAG repeat domain. The particular length of the CAG repeat domain may vary with the respect to the specific target gene so long as it results in deleterious activity, and in some instances is 25 repeats or longer, such as 30 repeats or longer, including 35 repeats or longer. Specific target genes, diseases associated therewith and the specific length of repeat sequences of extended CAG repeats, include (but are not limited to) those provided in Table 1, below.

TABLE 1

| Disease | | Gene name/protein product | Pathogenic repeat length |
|---|---|---|---|
| Spinocerebellar ataxia type 1 | SCA1 | SCA1/ataxin 1 | 40~82 |
| Spinocerebellar ataxia type 2 | SCA2 | SCA2/ataxin 2 | 32~200 |
| Spinocerebellar ataxia type 3 | SCA3(MJD) | SCA3/ataxin 3 | 61~84 |
| Spinocerebellar ataxia type 7 | SCA7 | SCA7/ataxin 7 | 37~306 |
| Spinocerebellar ataxia type 17 | SCA17 | SCA17/TBP | 47~63 |
| Dentatorubral pallidoluysian atrophy | DRPLA | DRPLA/atrophin 1 | 49~88 |
| Spinal and bular muscular atrophy | SBMA | AR/androgen receptor | 38~62 |
| Huntington's disease | HD | Htt/huntingtin | 40~121 |

Depending on the particular embodiments being practiced, a variety of different types of active agents may be employed. In some instances, the agent modulates the activity of the protein following expression, such that the agent is one that changes the activity of the protein encoded by the target gene following expression of the protein from the target gene. In these instances, the agent is one that may act directly with protein encoded by the target gene. In these instances, the agent may be one that selectively reduces the deleterious activity, e.g., aggregation, of the encoded protein, but retains or enhances, at least to a detectable level, the beneficial activity of the encoded protein. In certain embodiments, such agents are not inhibitors of aggregation of the protein, but instead selectively reduce the deleterious activity of the protein via another mechanism, e.g., by reducing the amount of the protein in the cell that is available for aggregation, by reducing production of a protein that is detrimental to cells independently of its propensity to aggregate, by preventing mis-folding of the encoded protein, etc.

In yet other embodiments, the agent modulates expression of the RNA and/or protein from the gene, such that it changes the expression of the RNA or protein from the target gene in some manner. In these instances, the agent may change expression of the RNA or protein in a number of different ways, where agents of interest include selective SPT4 modulatory agents. Selective SPT4 modulatory agents are agents that selectively change the SPT4 activity in a cell, e.g., decrease SPT4 activity in a cell. In some instances, the target SPT4 activity that is modulated, e.g., decreased, by the active agent is a transcription activity, and specifically an activity that facilitates RNA polymerase II processivity through long trinucleotide repeat domains, e.g., long CAG repeat domains. The target SPT4 activity that is modulated by such agents is an activity arising from an SPT4 protein. The term SPT4 protein is used herein to collectively refer to not only yeast Spt4 proteins, but also mammalian homologs thereof, e.g., human SUPT4H; murine Supt4h, etc. As such, SPT4 proteins of interest whose activity may be modulated by the selective SPT4 modulatory agents include, but are not limited to: *S. cerevisiae* Spt4; human SUPT4H and murine Supt4h.

Where the agent employed in methods of the invention is an SPT4 modulatory agent, the modulatory agent that is employed may be any agent that, upon introduction into a cell, changes the SPT4 activity of the cell, and specifically reduces the extended trinucleotide repeat mediated SPT4 transcription activity in the subject. The SPT4 modulatory agent may modulate activity in a number of different ways, e.g., by reducing expression of an SPT4 protein, by inhibiting binding of an SPT4 protein to another protein, e.g., a protein interacting with SPT4 (e.g., an SPT5 protein, such as Spt5 or SUPT5H), etc. Examples of different types of modulatory agents are now reviewed in greater detail below.

In certain embodiments, the agent is one that reduces, including inhibits, expression of a functional SPT4 protein. Inhibition of SPT4 protein expression may be accomplished using any convenient means, including use of an agent that inhibits SPT4 protein expression, such as, but not limited to: antisense agents, RNAi agents, agents that interfere with transcription factor binding to a promoter sequence of the SPT4 gene, or inactivation of the SPT4 gene, e.g., through recombinant techniques, etc.

For example, antisense molecules can be used to down-regulate expression of an SPT4 gene in the cell. The anti-sense reagent may be antisense oligodeoxynucleotides (ODN), particularly synthetic ODN having chemical modifications from native nucleic acids, or nucleic acid constructs that express such anti-sense molecules as RNA. The antisense sequence is complementary to the mRNA of the targeted protein, and inhibits expression of the targeted protein. Antisense molecules inhibit gene expression through various mechanisms, e.g., by reducing the amount of mRNA available for translation, through activation of RNAse H, or steric hindrance. One or a combination of antisense molecules may be administered, where a combination may include multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996), *Nature Biotechnol.* 14:840-844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993), supra, and Milligan et al., supra.) Oligonucleotides may be chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH$_2$-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. (1995), *Nucl. Acids Res.* 23:4434-42). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. (1995), *Appl. Biochem. Biotechnol.* 54:43-56.

In addition, the transcription level of a SPT4 protein can be regulated by gene silencing using RNAi agents, e.g., double-strand RNA (Sharp (1999) *Genes and Development* 13: 139-141). RNAi, such as double-stranded RNA interference (dsRNAi) or small interfering RNA (siRNA), has been extensively documented in the nematode *C. elegans* (Fire, A., et al, *Nature,* 391, 806-811, 1998) and routinely used to "knock down" genes in various systems. RNAi agents may be dsRNA or a transcriptional template of the interfering ribonucleic acid which can be used to produce dsRNA in a cell. In these embodiments, the transcriptional template may be a DNA that encodes the interfering ribonucleic acid. Methods and procedures associated with RNAi are also described in WO 03/010180 and WO 01/68836, all of which are incorporated herein by reference. dsRNA can be prepared according to any of a number of methods that are known in the art, including in vitro and in vivo methods, as well as by synthetic chemistry approaches. Examples of such methods include, but are not limited to, the methods described by Sadher et al. (Biochem. Int. 14:1015, 1987); by Bhattacharyya (Nature 343:484, 1990); and by Livache, et al. (U.S. Pat. No. 5,795,715), each of which is incorporated herein by reference in its entirety. Single-stranded RNA can also be produced using a combination of enzymatic and organic synthesis or by total organic synthesis. The use of synthetic chemical methods enable one to introduce desired modified nucleotides or nucleotide analogs into the dsRNA. dsRNA can also be prepared in vivo according to a number of established methods (see, e.g., Sambrook, et al. (1989) Molecular Cloning: A Laboratory Manual, 2nd ed.; Transcription and Translation (B. D. Hames, and S. J. Higgins, Eds., 1984); DNA Cloning, volumes I and II (D. N. Glover, Ed., 1985); and Oligonucleotide Synthesis (M. J. Gait, Ed., 1984, each of which is incorporated herein by reference in its entirety). A number of options can be utilized to deliver the dsRNA into a cell or population of cells such as in a cell culture, tissue, organ or embryo. For instance, RNA can be directly introduced intracellularly. Various physical methods are generally utilized in such instances, such as administration by microinjection (see, e.g., Zernicka-Goetz, et al. (1997) Development 124:1133-1137; and Wianny, et al. (1998) Chromosoma 107: 430-439). Other options for cellular delivery include permeabilizing the cell membrane and electroporation in the presence of the dsRNA, liposome-mediated transfection, or transfection using chemicals such as calcium phosphate. A number of established gene therapy techniques can also be utilized to introduce the dsRNA into a cell. By introducing a viral construct within a viral particle, for instance, one can achieve efficient introduction of an expression construct into the cell and transcription of the RNA encoded by the construct.

In another embodiment, the SPT4 gene is inactivated so that it no longer expresses a functional protein. By inactivated is meant that the gene, e.g., coding sequence and/or regulatory elements thereof, is genetically modified so that it no longer expresses a functional SPT4 protein, e.g., at least with respect to SPT4 transcription activity through a region of extended trinucleotide repeats in a target gene. The alteration or mutation may take a number of different forms, e.g., through deletion of one or more nucleotide residues, through exchange of one or more nucleotide residues, and the like. One means of making such alterations in the coding sequence is by homologous recombination. Methods for generating targeted gene modifications through homologous recombination are known in the art, including those described in: U.S. Pat. Nos. 6,074,853; 5,998,209; 5,998, 144; 5,948,653; 5,925,544; 5,830,698; 5,780,296; 5,776, 744; 5,721,367; 5,614,396; 5,612,205; the disclosures of which are herein incorporated by reference.

Also of interest in certain embodiments are dominant negative mutants of SPT4 proteins, where expression of such mutants in the cell result in a modulation, e.g., decrease, in SPT4 mediated transcription of extended trinucleotide repeats in a cell. Dominant negative mutants of SPT4 are mutant proteins that exhibit dominant negative SPT4 activity. As used herein, the term "dominant-negative SPT4 activity" or "dominant negative activity" refers to the inhibition, negation, or diminution of certain particular activities of SPT4, and specifically to SPT4 mediated transcription of extended trinucleotide repeats. Dominant negative mutations are readily generated for corresponding proteins. These may act by several different mechanisms, including mutations in a substrate-binding domain; mutations in a catalytic domain; mutations in a protein binding domain (e.g. multimer forming, effector, or activating protein binding domains); mutations in cellular localization domain, etc. A mutant polypeptide may interact with wild-type polypeptides (made from the other allele) and form a non-functional multimer. In certain embodiments, the mutant polypeptide will be overproduced. Point mutations are made that have such an effect. In addition, fusion of different polypeptides of various lengths to the terminus of a protein, or deletion of specific domains can yield dominant negative mutants. General strategies are available for making dominant negative mutants (see for example, Herskowitz (1987) Nature 329:219, and the references cited above). Such techniques are used to create loss of function mutations, which are useful for determining protein function. Methods that are well known to those skilled in the art can be used to construct expression vectors containing coding sequences and appropriate transcriptional and translational control signals for increased expression of an exogenous gene introduced into a cell. These methods include, for example, in vitro recombinant DNA techniques, synthetic techniques, and in vivo genetic recombination. Alternatively, RNA capable of encoding gene product sequences may be chemically synthesized using, for example, synthesizers. See, for example, the techniques described in "Oligonucleotide Synthesis", 1984, Gait, M. J. ed., IRL Press, Oxford.

In yet other embodiments, the agent is an agent that modulates, e.g., inhibits, SPT4 activity by binding to SPT4 and/or inhibiting binding of SPT4 to a second protein, e.g., an SPT5 protein, such as Spt5 or SUPT5H. For example, small molecules that bind to the SPT4 and inhibit its activity (e.g., binding to an STP5 protein) are of interest. Naturally occurring or synthetic small molecule compounds of interest include numerous chemical classes, such as organic molecules, e.g., small organic compounds having a molecular weight of more than 50 and less than about 2,500 daltons. Candidate agents comprise functional groups for structural interaction with proteins, particularly hydrogen bonding, and typically include at least an amine, carbonyl, hydroxyl or carboxyl group, preferably at least two of the functional chemical groups. The candidate agents may include cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Such molecules may be identified, among other ways, by employing the screening protocols described below.

In practicing methods according to embodiments of the invention, an effective amount of the active agent, e.g., SPT4 modulatory agent, is provided in the target cell or cells. In some instances, the effective amount of the modulatory agent is provided in the cell by contacting the cell with the modulatory agent. Contact of the cell with the modulatory agent may occur using any convenient protocol. The protocol may provide for in vitro or in vivo contact of the modulatory agent with the target cell, depending on the location of the target cell. Contact may or may not include entry of the agent into the cell. For example, where the target cell is an isolated cell and the modulatory agent is an agent that modulates expression of SPT4, the modulatory agent may be introduced directly into the cell under cell culture conditions permissive of viability of the target cell. Such techniques include, but are not necessarily limited to: viral infection, transfection, conjugation, protoplast fusion, electroporation, particle gun technology, calcium phosphate precipitation, direct microinjection, viral vector delivery, and the like. The choice of method is generally dependent on the type of cell being contacted and the nature of the modulatory agent, and the circumstances under which the transformation is taking place (e.g., in vitro, ex vivo, or in vivo). A general discussion of these methods can be found in Ausubel, et al, Short Protocols in Molecular Biology, 3rd ed., Wiley & Sons, 1995.

Alternatively, where the target cell or cells are part of a multicellular organism, the modulatory agent may be administered to the organism or subject in a manner such that the agent is able to contact the target cell(s), e.g., via an in vivo or ex vivo protocol. By "in vivo," it is meant in the target construct is administered to a living body of an animal. By "ex vivo" it is meant that cells or organs are modified outside of the body. Such cells or organs are typically returned to a living body.

In the subject methods, the active agent(s) may be administered to the targeted cells using any convenient administration protocol capable of resulting in the desired activity. Thus, the agent can be incorporated into a variety of formulations, e.g., pharmaceutically acceptable vehicles, for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments (e.g., skin creams), solutions, suppositories, injections, inhalants and aerosols. As such, administration of the agents can be achieved in various ways, including oral, buccal, rectal, parenteral, intraperitoneal, intradermal, transdermal, intracheal, etc., administration.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Where the agent is a polypeptide, polynucleotide, analog or mimetic thereof, it may be introduced into tissues or host cells by any number of routes, including viral infection, microinjection, or fusion of vesicles. Jet injection may also be used for intramuscular administration, as described by Furth et al. (1992), *Anal Biochem* 205:365-368. The DNA may be coated onto gold microparticles, and delivered intradermally by a particle bombardment device, or "gene gun" as described in the literature (see, for example, Tang et al. (1992), *Nature* 356:152-154), where gold microprojectiles are coated with the DNA, then bombarded into skin cells. For nucleic acid therapeutic agents, a number of different delivery vehicles find use, including viral and non-viral vector systems, as are known in the art.

Those of skill in the art will readily appreciate that dose levels can vary as a function of the specific compound, the nature of the delivery vehicle, and the like. Preferred dosages for a given compound are readily determinable by those of skill in the art by a variety of means.

As reviewed above, the subject methods result in selective reduction in the deleterious activity of an extended trinucleotide repeat gene in a target cell or cells, where the target cell(s) may be in vitro or in vivo. In certain embodiments, the subject methods result in reduction in toxicity of a target gene, e.g., via a reduction in aggregation of a protein encoded thereby, in a target cell(s). In certain embodiments, the methods result in enhancement in function of a protein encoded by a target gene.

The above methods find use in a variety of different applications. Certain applications are now reviewed in the following Utility section.

Utility

The subject methods find use in a variety of applications in which reduction of the deleterious activity of gene containing a mutant extended trinucleotide repeat domain is desired. As such, aspects of the invention include reducing toxicity of and/or enhancing functionality of a protein encoded by such a gene, as described herein, in any subject in need thereof, e.g., a subject that has been diagnosed with a condition that can be treated by effecting one or more of the above outcomes in the subject. Of interest is use of the methods and compositions of the invention to modify the progression of disease conditions associated with the deleterious activity of genes containing mutant extended trinucleotide repeat domains. The phrase "modify the progression" is employed to encompass both reduction in rate of progression (e.g., as manifested in the delay of the occurrence of one or more symptoms of the disease condition), as well as reversal of progression, including cure, of a disease condition (e.g., as manifested in the reduction of magnitude of one or more symptoms of the disease condition). Specific disease conditions in which the methods and compositions of the invention find use include, but are not limited to polyQ disease conditions, such as Spinocerebellar ataxia type 1, Spinocerebellar ataxia type 2, Spinocerebellar ataxia type 3, Spinocerebellar ataxia type 7, Spinocerebellar ataxia type 17, Dentatorubral pallidoluysian atrophy, Spinal and bular muscular atrophy, and Huntington's Disease.

In some instances, practice of methods of the invention results in treatment of a subject for a disease condition. By treatment is meant at least an amelioration of one or more symptoms associated with the disease condition afflicting the subject, where amelioration is used in a broad sense to refer to at least a reduction in the magnitude of a parameter, e.g., symptom, associated with the pathological condition being treated, such as loss of cognitive function, etc. As such, treatment also includes situations where the pathological condition, or at least symptoms associated therewith, are completely inhibited, e.g., prevented from happening, or stopped, e.g., terminated, such that the subject no longer suffers from the pathological condition, or at least the symptoms that characterize the pathological condition.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

Screening Assays

Aspects of the invention also include screening assays configured to identify agents that find use in methods of the invention, e.g., as reviewed above. Screening assays of interest include methods of assessing whether a test compound modulates the activity of a protein encoded by a gene comprising mutant extended trinucleotide repeat domain. By assessing is meant at least predicting that a given test compound will have a desirable activity, such that further testing of the compound in additional assays, such as animal model and/or clinical assays, is desired. The identification of the role of SPT4 proteins in transcription of genes containing mutant extended trinucleotide repeats allows in vitro reconstruction of the pathway. Two or more of the pathway components, e.g., an SPT4 and an SPT5 protein, may be combined in vitro, and the behavior in the presence of the test compound assessed in a number of different ways, e.g., in production of a signal which only occurs upon interaction of pathway components, in terms of activation of transcription of specific target sequences, etc.

Drug screening may be performed using an in vitro model, a genetically altered cell or animal, or purified SPT4 protein. One can identify ligands or substrates that compete with, modulate or mimic the action of SPT4 protein. Drug screening identifies agents that mimic SPT4 activity, either as an antagonist or as an agonist. A wide variety of assays may be used for this purpose, including labeled in vitro protein-protein binding assays, electrophoretic mobility shift assays, immunoassays for protein binding, and the like. Knowledge of the 3-dimensional structure of SPT4, derived from crystallization of purified synthetic SPT4 protein, leads to the rational design of small drugs that specifically inhibit SPT4 activity.

The term "agent" as used herein describes any molecule, e.g., protein or pharmaceutical, with the capability of altering or mimicking the physiological function of an SPT4 protein. Generally, a plurality of assay mixtures are run in parallel with different agent concentrations to obtain a differential response to the various concentrations. Typically one of these concentrations serves as a negative control, i.e., at zero concentration or below the level of detection.

Candidate agents encompass numerous chemical classes, such as organic molecules, e.g., small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Of interest in certain embodiments are compounds that pass the blood-brain barrier.

Where the screening assay is a binding assay, one or more of the molecules may be joined to a member of a signal producing system, e.g., a label, where the label can directly or indirectly provide a detectable signal. Various labels include, but are not limited to: radioisotopes, fluorescers, chemiluminescers, enzymes, specific binding molecules, particles, e.g., magnetic particles, and the like. Specific binding molecules include pairs, such as biotin and streptavidin, digoxin and antidigoxin, etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc. that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components is added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

The compounds having the desired pharmacological activity may be administered in a physiologically acceptable carrier to a host for treatment or prevention of a disease associated with activity of a gene containing extended trinucleotide repeats. The agents may be administered in a variety of ways, orally, topically, parenterally e.g., subcutaneously, intraperitoneally, by viral infection, intravascularly, etc. Depending upon the manner of introduction, the compounds may be formulated in a variety of ways. The concentration of therapeutically active compound in the formulation may vary from about 0.1-10 wt %.

In some instances, the methods include screening the compound with a cell which includes a signal producing system operatively coupled to an SPT4 protein to assess whether the compound modulates the activity of the protein encoded by a gene comprising a mutant extended trinucleotide repeat domain. A signal producing system is operatively coupled to an SPT4 protein if the signal produced by the signal producing system, e.g., fluorescent signal, conversion of substrate to a detectable product, etc., occurs or does not occur depending on an activity of an SPT4 protein, e.g., ability of the SPT4 protein to bind to a second protein, such as an SPT5 protein, ability of an SPT4 protein to assist in transcription of a mutant trinucleotide repeat domain, etc. Accordingly, the signal producing system present in the cell may be one that produces a signal in an SPT4 transcriptional activity dependent manner.

Of interest are assays in which the signal producing system produces a signal in an SPT4/SPT5 protein complex formation dependent manner. An example of such an assay is where SPT4 is labeled with a first member of a signal producing system (e.g., where the signal producing system comprises a fusion of an SPT4 protein and a signal producing system label) and SPT5 is labeled with a second member of a signal producing system and complex formation of the SPT4 and SPT5 proteins results in proximity of the first and second signal producing system members to provide a signal, either directly or indirectly. An example of such a system is a FRET assay, which the first member of a signal producing system is a donor fluorescent moiety and the second member of the signal producing system is an acceptor fluorescent moiety. By screening for the fluorescent emission of the acceptor fluorescent moiety, such assays can be employed to assess whether a candidate agent interferes with binding of an SPT4 protein to an SPT5 protein. Any convenient FRET protocol may be employed, where protocols and specific labels of interest that may be readily adapted for assays of the invention include, but are not limited to: those described in U.S. Pat. Nos. 7,749,759; 7,718,766; 7,709,608; 7,678,550; 7,674,588; 7,495,069; 7,413,862; 7,332,567; 7,208,285; 7,183,066; 7,160,998;

6,908,769; 6,642,001 and 6,376,257; the disclosures of protocols and labels presented in these patents being incorporated herein by reference.

Another type of assay of interest that that produces a signal in an SPT4 transcriptional activity dependent manner is one in which the protein encoded by the target gene comprises a signal producing system domain. In such assays, the target gene which includes the mutant extended trinucleotide repeat also includes a coding sequence for a protein that is a member of the signal producing system. Examples of such proteins includes fluorescent proteins, enzymes, etc. In such assays, agents which restore function to a label protein encoded by a target gene having a mutant extended trinucleotide repeat can be readily identified by assays for function of the signal producing system protein, e.g., fluorescent emission from the protein, enzymatic activity from the protein. Examples of such assays include the GFP and ADE2 based assays described in greater detail in the experimental section. In such assays, the target gene employed in the assay includes a coding sequence for the label protein operatively linked to a mutant extended trinucleotide repeat domain. Additional examples of fluorescent proteins of interest that may be employed as signal producing system labels include, but are not limited to, reef coral fluorescent proteins, e.g., as available under the Living Colors trademark from Clontech laboratories, and the like. Additional examples of enzymatic labels of interest include, but are not limited to: luciferase, SEAP, horse radish peroxidase, β-galactosidase, etc. Of interest in some instances are non-invasive whole animal in vivo assays, such as those described in U.S. Pat. Nos. 7,255,851; 7,198,774; 6,939,533; 6,923,951; 6,916,462; 6,908,605; 6,890,515; 6,649,143; 6,217,847; and 5,650,135; the disclosures of which are herein incorporated by reference. Also of interest is the color colony assay described in U.S. Pat. No. 7,375,190, the entire content of which is incorporated herein by reference.

As such, aspects of the invention further include screening assays designed to find SPT4 pathway modulatory agents, where such agents may find use in a variety of applications, including as therapeutic agents, as described above, e.g., for treatment or prevention of conditions arising from the activity of a gene containing extended trinucleotide repeats. The screening methods may be assays which provide for qualitative/quantitative measurements of SPT4 activity in the presence of a particular candidate therapeutic agent. The screening method may be an in vitro or in vivo format.

Combination Therapies

Active agents of the invention can be supplied alone or in combination with one or more other active agents. For example, selective SPT4 inhibitory agents can be supplied alone or in conjunction with one or more other drugs, such as drugs employed in the treatment of polyQ diseases. Possible combination partners can include, e.g., Tetrabenazine (Xenazine); Antipsychotic drugs, such as haloperidol (Haldol) and clozapine (Clozaril); antiseizure drugs such as clonazepam (Klonopin) and antianxiety drugs such as diazepam (Valium); antidepressants including such drugs as escitalopram (Lexapro), fluoxetine (Prozac, Sarafem) and sertraline (Zoloft); and the like.

Pharmaceutical Preparations

Also provided are pharmaceutical preparations of the subject compounds. The subject compounds can be incorporated into a variety of formulations for administration to a subject. More particularly, the compounds of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. The formulations may be designed for administration via a number of different routes, including oral, buccal, rectal, parenteral, intraperitoneal, intradermal, transdermal, intracheal, etc., administration.

In pharmaceutical dosage forms, the compounds may be administered in the form of their pharmaceutically acceptable salts, or they may also be used alone or in appropriate association, as well as in combination, with other pharmaceutically active compounds. The following methods and excipients are merely exemplary and are in no way limiting.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethyl-cellulose, methylcellulose, hydroxy-propylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate.

The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

The compounds of this invention and their pharmaceutically acceptable salts which are active on topical administration can be formulated as transdermal compositions or transdermal delivery devices ("patches"). Such compositions include, for example, a backing, active compound reservoir, a control membrane, liner and contact adhesive. Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference in its entirety. Such patches may be constructed for continuous, pulsatile, or on demand delivery of pharmaceutical agents.

Optionally, the pharmaceutical composition may contain other pharmaceutically acceptable components, such a buffers, surfactants, antioxidants, viscosity modifying agents, preservatives and the like. Each of these components is well-known in the art. See, for example, U.S. Pat. No. 5,985,310, the disclosure of which is herein incorporated by reference.

Other components suitable for use in the formulations of the present invention can be found in Remington's Pharmaceutical Sciences, Mace Publishing Company, Philadelphia, Pa., 17th ed. (1985). In an embodiment, the aqueous cyclodextrin solution further comprise dextrose, e.g., about 5% dextrose.

Dosage levels of the order of from about 0.01 mg to about 140 mg/kg of body weight per day are useful in representative embodiments, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day. Those of skill will readily appreciate that dose levels can vary as a function of the specific compound, the severity of the symptoms and the susceptibility of the subject to side effects. Dosages for a given compound are readily determinable by those of skill in the art by a variety of means.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

As such, unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier. The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular peptidomimetic compound employed and the effect to be achieved, and the pharmacodynamics associated with each compound in the host.

Kits & Systems

Also provided are kits and systems that find use in practicing embodiments of the methods, such as those described as described above. The term "system" as employed herein refers to a collection of two or more different active agents, present in a single or disparate composition, that are brought together for the purpose of practicing the subject methods. The term kit refers to a packaged active agent or agents. For example, kits and systems for practicing the subject methods may include one or more pharmaceutical formulations. As such, in certain embodiments the kits may include a single pharmaceutical composition, present as one or more unit dosages, where the composition may include one or more expression/activity inhibitor compounds. In yet other embodiments, the kits may include two or more separate pharmaceutical compositions, each containing a different active compound.

Also of interest are kits and systems finding use in assays of the invention, e.g., as described above. Such kits and systems may include one or more components of the assays, e.g., vectors encoding fusion proteins, enzyme substrates, buffers, etc.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

The following examples are offered by way of illustration and not by way of limitation.

EXPERIMENTAL

I. Materials and Methods
A. Yeast Strains

All strains were constructed by the one-step gene disruption method and confirmed by genomic PCR as described previously (Cheng, T. H., and Gartenberg, M. R. (2000). Yeast heterochromatin is a dynamic structure that requires silencers continuously. Genes Dev 14, 452-46). hsp104Δ and spt4Δ were derived from parental W303-1A cells by replacing respective HSP104 (chromosome XII, coordinates 88622-91348) and SPT4 (chromosome VII, coordinates 617828-617520) genes with a PCR-amplified KanMX gene. Similarly, thp2Δ was generated by replacing THP2 gene (chromosome VIII, coordinates 439344-440129) with a HIS3 marker gene.

B. Plasmids

The pYES2-ADE2 construct has been described previously (Ghukasyan, V., Hsu, C. C., Liu, C. R., Kao, F. J., and Cheng, T. H. (2010). Fluorescence lifetime dynamics of enhanced green fluorescent protein in protein aggregates with expanded polyglutamine. J Biomed Opt 15, 016008), and pYES2-25Q-eGFP and pYES2-97Q-eGFP plasmids containing a stretch of (CAG CAG CAA CAG CAA CAA), (SEQ ID NO:07) encoding polyglutamine residues (Meriin, A. B., Zhang, X., He, X., Newnam, G. P., Chernoff, Y. O., and Sherman, M. Y. (2002). Huntington toxicity in yeast model depends on polyglutamine aggregation mediated by a prion-like protein Rnq1. J Cell Biol 157, 997-1004) were kindly provided by Dr. Michael Sherman. The ADE2 open reading frame was PCR-amplified using pYES2-ADE2 as template and then used to replace eGFP in pYES2-25Q-eGFP and pYES2-97Q-eGFP to create pYES2-25Q-ADE2 and pYES2-97Q-ADE2, respectively. Resultant constructs expressed N-terminally FLAG-tagged polyQ-ADE2 under control of the galactose-inducible promoter Gal1. Reporter genes were subsequently subcloned into pRS424. SPT4 along with its endogenous promoter (chromosome VII, coordinates 618321-617353) was amplified by PCR using yeast genomic DNA as template and then cloned into pRS415 to generate pRS415-SPT4. RNQ1-GFP plasmid was obtained from Dr. Chih-Yen King. Constructs expressing polyQ-ADE2 or polyQ-eGFP with $(CAG)_n$ repeats were derived from pYES2-eGFP (Ghukasyan et al., 2010, supra). Oligonucleotides, 5'-p-CAGCAGCAGCAGCAGCAG-3' (SEQ ID NO:01) and 5'-p-CTGCTGCTGCTGCTGCTG-3' (SEQ ID NO:02), were mixed and annealed at room temperature, ligated, PCR-amplified, and cloned into the pYES2-eGFP Sma I site to generate pYES2-$(CAG)_n$-eGFP. CAG fragments were released from these constructs by Kpn I and Bam HI digestion and cloned into pYES2-25Q-ADE2 digested with the same restriction enzymes to create pYES2-$(CAG)_n$-ADE2. Reporter genes were also subcloned into pRS424. To express polyQ-eGFP in mammalian cells, the corresponding DNA fragments were PCR-amplified using various forms of pYES2-$(CAG)_n$-eGFP as templates and cloned into pTRE2hyg2-HA (BD Biosciences) to create pTRE2-$(CAG)_n$-eGFP. All constructs were confirmed by DNA sequencing.

C. Yeast Genome-wide Screening and Identification of Suppressors

Random transposon-mediated mutagenesis was carried out as described on the website of Dr. Snyder's laboratory (website at the address formed by placing "http://" before "snyderlab.stanford.edu"). Briefly, a mTn-lacZ/LEU2 insertion library was digested with Not I and used to transform W303-1A cells harboring pRS424-97Q-ADE2. Transformants were recovered in rich YPDA medium for 2 hr and spread on appropriate selection plates. Cells were incubated at 30° C. for 3 days and then replicated to plates that contain galactose (2%) and limiting adenine (4 μg/ml). After development of yeast colony color, candidates (white or pink colonies) were picked and polyQ-Ade2 protein solubility was confirmed by a filter-trap assay. More than 150,000 transformants were subjected to this screening.

The site of transposon insertion was identified by inverse PCR (Scholes, D. T., Banerjee, M., Bowen, B., and Curcio, M. J. (2001)). Multiple regulators of Ty1 transposition in *Saccharomyces cerevisiae* have conserved roles in genome maintenance. Genetics 159, 1449-1465. Genomic DNA of candidate clones was isolated and digested with Rsa I, followed by DNA ligation and PCR amplification using the inverse primer set IN1 and IN2, followed by DNA sequencing using the SEQ primer (Table 51, below).

D. Antibodies

Antibodies against α-tubulin (DM1A, Sigma), FLAG-epitope (M5, F4042, Sigma), Hsp104 (ab2924, Abcam), GFP (ab6556, Abcam), Supt4h (ab54350, Abcam), superoxide dismutase MnSOD (DD-17, Sigma), Huntingtin (MAB2166, chemicon), and TATA-binding protein (58C6, Sigma) were purchased. Monoclonal anti-RNA polymerase II antibody (4H8-ChIP grade, Abcam), used for chromatin immunoprecipitation, was also purchased.

E. Biochemical Analysis

To prepare yeast lysates, 10 $OD_{600}$ of cells were collected, suspended in ESB buffer (2% SDS, 80 mM Tris-HCl [pH 6.8], 10% glycerol, 1.5% DTT) supplemented with 1 mM $Na_3VO_4$, 1 mM DTT, 1 mM PMSF and a protease inhibitor cocktail (Sigma), followed by grinding in glass beads. The supernatant was collected as crude lysate after low speed centrifugation (600 g). All steps were performed at 4° C. Cultured neurons were lysed with RIPA buffer (50 mM Tris-HCl [pH 7.5], 150 mM NaCl, 1% NP-40, 0.1% SDS and 1% sodium deoxycholate) supplemented with 1 mM $Na_3VO_4$, 1 mM DTT, 1 mM PMSF and a protease inhibitor cocktail.

Crude lysates were diluted 100-fold with TBS buffer (20 mM Tris HCl [pH7.5], 500 mM NaCl), and then loaded onto a 0.2 μm cellulose acetate membrane for the filter-trap assay or 0.45 μm nitrocellulose membranes for a slot blot assay. Following two TBST (TBS with 0.05% Tween 20) rinses, membranes were removed from the Bio-Dot (Bio-Rad) apparatus and blocked with PBS-T (1×PBS, 0.2% Triton X-100) containing 5% non-fat dry milk, probed with primary antibodies for 1 hr, washed three times with PBS-T for 15 min, and incubated with appropriate secondary antibodies conjugated to horseradish peroxidase for another 1 hr. After three 15 min PBS-T washes, signals were detected using Western Lighting (PerkinElmer Life Sciences).

Equal quantities (10 or 15 μg) of protein lysate separated on SDS-polyacrylamide gels, followed by transfer to nitrocellulose membranes. Immunoblotting was performed essentially as described above. To analyze huntingtin variants, Tris-acetate polyacrylamide gels were used to obtain greater resolution (Hu, J., Matsui, M., Gagnon, K. T., Schwartz, J. C., Gabillet, S., Arar, K., Wu, J., Bezprozvanny, I., and Corey, D. R. (2009). Allele-specific silencing of mutant huntingtin and ataxin-3 genes by targeting expanded CAG repeats in mRNAs. Nat Biotechnol 27, 478-484).

F. Northern Blotting

Yeast total RNA was isolated using the hot acid phenol method (Cheng and Gartenberg, 2000, supra). 15 μg RNA from each sample was loaded and separated on 1% agarose gels, followed by transfer to a Nylon membrane (Schleicher & Schuell). The membrane was hybridized as per the manufacturer's suggestions (DIG Northern Starter Kit, Roche) using polyQ and SCR1 probes labeled by PCR DIG Probe Synthesis Kit (Roche).

G. Chromatin Immunoprecipitation (ChIP)

ChIP was performed as described (Cheng and Gartenberg, 2000, supra) with the following modifications. Cells were harvested (50 $OD_{600}$) after culturing in 2% galactose medium for 12 hr. Following formaldehyde fixation, cells were treated with zymolyase in 1.2 M sorbital 1 hr to facilitate cell lysis. Chromatin was collected, washed with 0.1×TE buffer, and fragmented using micrococcal nuclease (New England Biolabs). Chromatin associating with RNA polymerase II was precipitated by anti-RNA polymerase antibody (Abcam) bound to protein A agarose beads (Upstate). Washing buffer 3 (10 mM Tris-HCl [pH 8.0], 0.5 M LiCl, 1% NP-40, 0.5% sodium deoxycholate, 1 mM EDTA, and 0.05% SDS) was modified to increase stringency. PCR primer sets (TRP1-5' and TRP1-3' for the TRP1 promoter; ChIP prom-5' and ChIP prom-3' for the GAL1 promoter; ChIP dn500-5' and ChIP dn500-3' for the DNA region 500 bp downstream of the CAG repeat; ChIP dn1000-5' and ChIP dn1000-3' for the DNA region 1000 bp away from the CAG repeat) were used to amplify respective DNA domains. Oligonucleotide sequences are listed in Supplementary Table S1, below.

H. Cell Culture and Transfection

Murine striatal neural cell lines ST14A (rat), $Hdh^{Q7/Q7}$ (mouse), $Hdh^{Q111/Q111}$ (mouse), and $Hdh^{Q7/Q111}$ (mouse) were cultured in Dulbecco's modified Eagle's medium (SH30022, HyClone) supplemented with 10% fetal bovine serum (FBS) at 33° C. with 5% $CO_2$. ST14A was transfected with pTet-Off plasmid (BD Biosciences) to establish the stable cell line ST14A$^{tet}$, which expressed pTRE2-(CAG)$_n$-eGFP in the absence of tetracycline. DNA and siRNA transfections were carried out using LipofectAMINE 2000 (Invitrogen). 100 nM of Supt4h siRNA (DHARMACON, ON-TARGET plus SMART pool, L-048866-01) and (DHARMACON, J-086342-10, 5'-UGGCCUACAAAUC-GAGAGAUU-3'(SEQ ID NO:03) and 5'-UCUCUC-GAUUUGUAGGCCAUU-3' (SEQ ID NO:04)) were used to inhibit expression of Supt4h in mice and rat cells, respectively. Transfection of an equivalent amount of annealed double-stranded oligonucleotides (5'-UUCUC-CGAACGUGUCACGUTT-3' (SEQ ID NO:05) and 5'-ACGUGACACGUUCGGAGAATT-3' (SEQ ID NO:06)) that do not target any gene served as a control.

I. Microscopy

As described (King, C. Y., Wang, H. L., and Chang, H. Y. (2006). Transformation of yeast by infectious prion particles. Methods 39, 68-71), yeast cells were transformed with RNQ1-GFP plasmid, followed by culture in growth medium containing 100 nM $CuSO_4$ to monitor [PIN$^+$] prions. PolyQ-eGFP aggregate formation was monitored post gene induction by culturing yeast cells in medium with 2% galactose. At 2, 4, and 8 hr time points, cells were mounted on an agarose pad on a single cavity slide and visualized using the Axioskop 2 (Carl Zeiss) fluorescence microscope with a 100× oil immersion objective. Differential interference contrast (DIC) images were taken for phase contrast. Similarly, for ST14A$^{tet}$, cells were seeded on coverslips and co-transfected with siRNA and poly-eGFP plasmid constructs. Imaging was performed at 24 hr.

J. Cell Viability

This assay was performed as described (Varma, H., Voisine, C., DeMarco, C. T., Cattaneo, E., Lo, D. C., Hart, A. C., and Stockwell, B. R. (2007). Selective inhibitors of death in mutant huntingtin cells. Nat Chem Biol 3, 99-100.) with minor modifications. ST14A$^{tet}$ cells were plated into 12-well plates at a density of $1\times10^5$/well. Following co-transfection of siRNA and pTRE2-(CAG)$_n$-eGFP plasmid constructs (7Q or 81Q), cells were incubated at 33° C. for 36 hr. Cultures were washed with HBSS, the medium was replaced with one containing low serum (0.5% FBS), and cells were incubated at 39° C. On the 4$^{th}$ day, cells were trypsinized and the number of viable cells was counted using the trypan blue dye exclusion method.

K. Reverse Transcription-PCR and Quantitative RT-PCR

Total RNA was isolated using TRI reagent (Sigma), and an equal amount (5 μg) of RNA from each sample was converted to cDNA by reverse transcriptase (SuperScript II, Invitrogen). Briefly, RNA was mixed with 5 μM oligo dT, 5 μM SnRNA U6 rt-PCR primer, and 500 μM dNTPs. The mixture was incubated at 65° C. for 5 min and then chilled on ice. After addition of First-Strand Buffer, DTT ($C_f$=10 mM) and 1 μL reverse transcriptase, the reaction was carried out at 42° C. for 1 hr. Equivalent volumes of cDNA products were amplified by PCR and products were resolved on 2.5% agarose gels to determine relative transcript levels with SnRNA U6 serving as control. PCR primer sets are shown in supplementary Table S1. Quantitative real-time PCR was performed using a StepOnePlus Real Time PCR system (Applied Biosystem) and analyzed using the Quantitative-Comparative $C_T$ ($\Delta\Delta C_T$) program.

L. Primers

Supplementary Table S1
A summary of oligonucleotide primers used in experiments in this study

| Inverse PCR | sequence | SEQ ID NO |
| --- | --- | --- |
| IN1 primer | 5'-TAAGTTGGGTAACGCCAGGGTTTTC-3' | (SEQ ID NO: 8) |
| IN2 primer | 5'-TTCCATGTTGCCACTCGCTTTAATG-3' | (SEQ ID NO: 9) |
| SEQ primer | 5'-CCCCCTTAACGTGAGTTTTCGTTCCACT-3' | (SEQ ID NO: 10) |
| Northern blot probes | sequence | |
| polyQ-5' primer | 5'-ACTACAAGGACGACGATGAC-3' | (SEQ ID NO: 11) |
| polyQ-3' primer | 5'-CCTCCTAATATACCAACTGTTC-3' | (SEQ ID NO: 12) |
| SCR1-5' primer | 5'-GGCTGTAATGGCTTTCTGGTG-3' | (SEQ ID NO: 13) |
| SCR1-3' primer | 5'-ACCAGACAGAGAGACGGATTC-3' | (SEQ ID NO: 14) |
| ChIP | sequence | |
| TRP1-5' primer | 5'-GATGGCAGTAGTGGAAGATATTC-3' | (SEQ ID NO: 15) |
| TRP1-3' primer | 5'-CAATGGACCAGAACTACCTGTG-3' | (SEQ ID NO: 16) |
| ChIP prom-5' primer | 5'-TTTTCGGTTTGTATTACTTCTTATTC-3' | (SEQ ID NO: 17) |
| ChIP prom-3' primer | 5'-GAAGGCCTTCATCAGCTTTTC-3' | (SEQ ID NO: 18) |
| ChIP dn500-5' primer | 5'-TCCGGAAGCTTTGGAAGTACTG-3' | (SEQ ID NO: 19) |
| ChIP dn500-3' primer | 5'-TAAGTTGAACGGAGTCCGGAAC-3' | (SEQ ID NO: 20) |
| ChIP dn1000-5' primer | 5'-GGTTCCTCAGTGTACTTATATGG-3' | (SEQ ID NO: 21) |
| ChIP dn1000-3' primer | 5'-TTTAAAACCGCACATGCGGCAG-3' | (SEQ ID NO: 22) |
| qPCR | sequence | |
| Tuba1a rtPCR-5' primer | 5'-CCATTGGCAAGGAGATCATTG-3' | (SEQ ID NO: 23) |
| Tuba1a rtPCR-3' primer | 5'-ATGGCCTCATTGTCTACCATG-3' | (SEQ ID NO: 24) |
| Tuba1a qPCR-3' primer | 5'-CTTTCCGTAATCCACAGAGAG-3' | (SEQ ID NO: 25) |
| Supt4 rtPCR-5' primer | 5'-TCATTGCGATGATGAGTCCAG-3' | (SEQ ID NO: 26) |
| Supt4 rtPCR-3' primer | 5'-TTTCGTGGAGTCTGCTGATTC-3' | (SEQ ID NO: 27) |
| Supt4 qPCR-3' primer | 5'-GCTGTGTCTCTGGATTTGTAG-3' | (SEQ ID NO: 28) |
| Htt rtPCR-5' primer | 5'-TCCTGATCAGTGAAGTGGTTC-3' | (SEQ ID NO: 29) |
| Htt rtPCR-3' primer | 5'-GTCACACTCCAACACATAGAG-3' | (SEQ ID NO: 30) |
| SnRNA U6 rt-PCR primer | 5'-AAAAATATGGAACGCTTCACGA-3' | (SEQ ID NO: 31) |
| SnRNA U6-5' primer | 5'-CTCGCTTCGGCAGCACATAT-3' | (SEQ ID NO: 32) |
| SnRNA U6-3' primer | 5'-TATGGAACGCTTCACGAATTTG-3' | (SEQ ID NO: 33) |

II. Results

Proteins containing long polyQ stretches are believed to be inherently prone to misfolding and consequent aggregation, and the loss of activity of such proteins has been attributed to such events (Krobitsch, S., and Lindquist, S. (2000). Aggregation of huntingtin in yeast varies with the length of the polyglutamine expansion and the expression of chaperone proteins. Proc Natl Acad Sci USA 97, 1589-1594; Ordway, J. M., Tallaksen-Greene, S., Gutekunst, C. A., Bernstein, E. M., Cearley, J. A., Wiener, H. W., Dure, L. S. t., Lindsey, R., Hersch, S. M., Jope, R. S., et al. (1997). Ectopically expressed CAG repeats cause intranuclear inclusions and a progressive late onset neurological phenotype in the mouse. Cell 91, 753-763). To discover possible cellular functions that restore activity to long-polyQ proteins, we established a genetic system that enables color-based identification of mutant yeast clones in which a yeast protein engineered to include extended polyQ repeats becomes enzymatically functional. Metabolic conversion of p-ribosylamino imidazole (AIR) to p-ribosylamino imidazole carbon/late (CAIR) is mediated in yeast by the Ade2 protein (Jones, E. W., and Fink, G. R. (1982). Regulation of amino acid and nucleotide biosynthesis in yeast. In The Molecular Biology of the Yeast *Saccharomyces*: Metabolism and Gene Expression, J. N. Strathern, Jones, E. W., & Broach, J. R., ed. (Cold Spring Harbor, N.Y., Cold Spring Harbor Laboratory Press), pp. p. 181-299): in yeast cells mutated chromosomally in ADE2, AIR accumulates and promotes a change in colony color from white to red (FIG. 1A). We constructed a series of plasmids that produce either wild-type Ade2 protein or protein containing either short or long repeats of polyQ (25Q-Ade2 or 97Q-Ade2, respectively) under control of a galactose-inducible promoter (FIG. 1B). The red color characteristic of ade2 deficiency was reversed by ectopic expression of the wild-type Ade2 protein or 25Q-Ade2, but not by expression of 97Q-Ade2—as indicated by the persistence of red-colored colonies produced by yeast expressing 97Q-Ade2 (FIG. 1C). However, in ade2 mutant yeast cells that also carry a mutation in the chaperonin protein Hsp104, which is known to be required for polyQ protein aggregation (Krobitsch and Lindquist, 2000, supra), we found that the 97Q-Ade2 protein was rendered biochemically active (FIG. 1C). A filter-trap assay (Scherzinger, E., Lurz, R., Turmaine, M., Mangiarini, L., Hollenbach, B., Hasenbank, R., Bates, G. P., Davies, S. W., Lehrach, H., and Wanker, E. E. (1997)). Huntingtin-encoded polyglutamine expansions form amyloid-like protein aggregates in vitro and in vivo. Cell 90, 549-558) confirmed the formation of 97Q-Ade2 protein aggregates in HSP104+ but not in hsp104Δ cells (FIG. 1D). As is characteristic of other proteins containing short polyQ repeats (Krobitsch and Lindquist, 2000, supra; Meriin et al., 2002, supra), aggregation of the 25Q-Ade2 protein was not observed in HSP104+ cells.

Figure 8A:
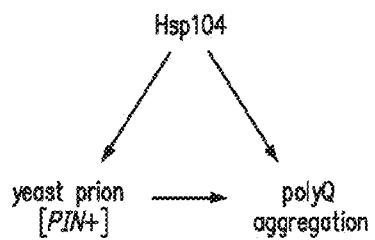
FIG. 8A-8C. Spt4 deficiency does not interfere with Hsp104 protein expression or yeast prions [PIN+], related to FIG. 1A-1G (FIG. 8A) A schematic diagram showing the relationship between Hsp104, yeast prion [PIN+] and polyQ aggregation. In yeast cells, polyQ aggregation requires prion [PIN+]. Hsp104 can facilitate polyQ aggregation and is essential for persistence of [PIN+].
Figure 8B:
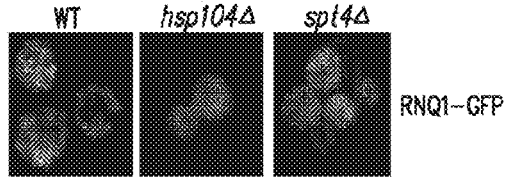
Figure 8C:
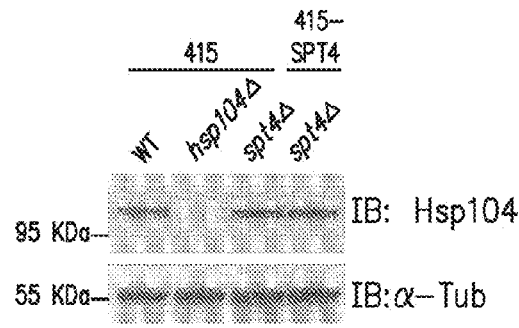
Figure 9A:
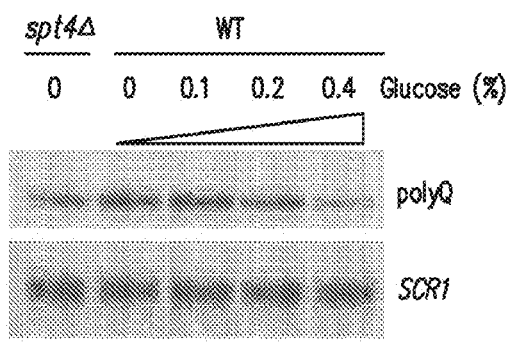
FIG. 9A-9C. Decreased 97Q-Ade2 gene transcription, resulting in reduced protein abundance, prevents polyQ protein aggregation, related to FIG. 2A-2F (FIG. 9A) WT cells, after raffinose pre-culturing, were grown in media with indicated glucose concentrations plus 2% galactose to induce 97Q-ADE2 gene expression under control of the GAL1 promoter. Progressively declining promoter activity is seen as glucose concentrations increase (Biggar, S. R., and Crabtree, G. R. (2001). Cell signaling can direct either binary or graded transcriptional responses. EMBO J 20, 3167-76). After 12 hr of induction, cells were collected and 97Q-ADE2 mRNA levels were analyzed by Northern blot using a polyQ probe. SCR1 transcript levels served as a loading control. 97Q-ADE2 mRNA expression in spt4D cells is shown for comparison.
Figure 9B:
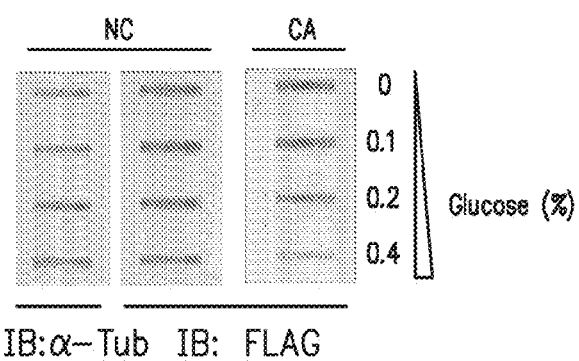
Figure 9C:
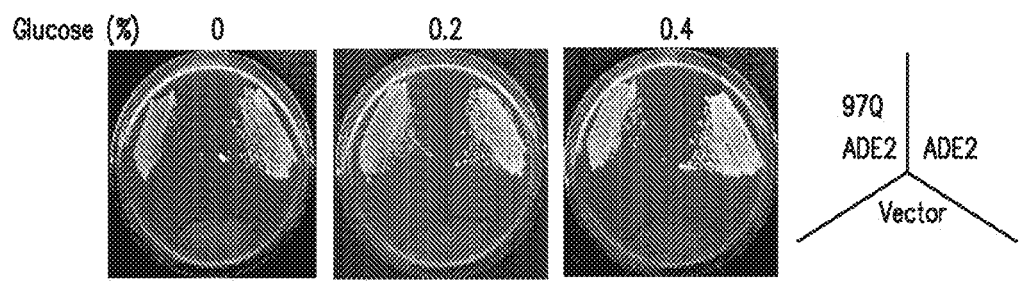

A. Identification of Yeast Mutations that Resume Activity of Protein Containing Long polyQ Expansions A phenotypic screen for *S. cerevisiae* mutations that enable the 97Q-Ade2 construct to produce an enzymatically active Ade2 protein was carried out using transposon insertion mutagenesis. This screen identified multiple clones in which colony color changed from red to pink or white. Inverse PCR DNA synthesis together with nucleotide sequencing determined that some of these clones not surprisingly contained a transposon inserted into genes encoding Hsp104 or [PIN+] prion protein Rnq1, both of which are known to be required for polyQ protein aggregation in yeast (Meriin et al., 2002, supra). However, our screen also detected a clone (clone 23-44) in which Hsp104 and Rnq1 were intact and further showed that in this clone the transposon had inserted into the gene encoding transcription elongation factor Spt4 (FIG. 1E), raising the prospect that loss of SPT4 function had enabled the 97Q-Ade2 construct to produce a functional 97Q-Ade2 protein. This hypothesis was confirmed by introducing a spt4 deletion (spt4Δ) into a strain containing the ade2-1 chromosomal mutation. As had been observed for clone 23-44, expression of the 97Q-Ade2 protein in the spt4Δ strain—which like clone 23-44 showed normal expression of Hsp104 protein and [PIN+] prion protein (FIG. 8)—resulted in both a light pink colony color and decreased formation of polyQ-dependent protein aggregates (FIGS. 1F and 1G).

B. SPT4 Mutation Diminishes Aggregation of Protein Containing Long Stretches of polyQ by Selectively Interfering with Transcription of mRNA Containing Multiple CAG Repeats spt4Δ cells showed reduced abundance of both 97Q-ADE2 mRNA and the polyQ protein encoded by these transcripts (FIGS. 2B and 2C). As the extent of aggregation of polyQ protein in vitro has been reported to be related to the protein concentration (Scherzinger, E., Sittler, A., Schweiger, K., Heiser, V., Lurz, R., Hasenbank, R., Bates, G. P., Lehrach, H., and Wanker, E. E. (1999). Self-assembly of polyglutamine-containing huntingtin fragments into amyloid-like fibrils: implications for Huntington's disease pathology. Proc Natl Acad Sci USA 96, 4604-4609), we wished to learn whether the decreased production of 97-Ade2 protein that we had observed in spt4 mutant yeast cells is sufficient to account for decreased aggregation of, and increased functionality of, the protein. We varied the extent of transcription of 97Q-ADE2 from the GAL1 promoter by altering the concentration of promoter-inhibiting glucose in the culture medium (FIG. 11). As 97Q-Ade2 expression declined, aggregation was correspondingly reduced, and the intensity of red color in 97Q-ADE2 expressing colonies decreased accordingly (FIG. 11). These findings show that the decreased aggregation and concurrent complementation of ade2 deficiency observed for the 97Q-Ade2 protein in spt4Δ cells was a consequence of reduction in the cellular concentration of the mutant protein.

Figure 10A:
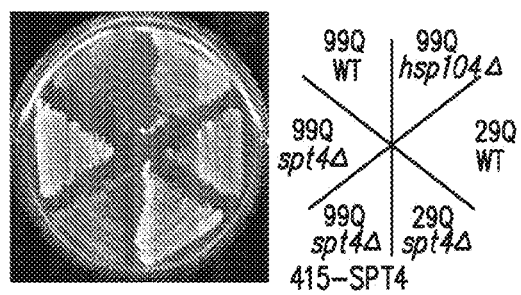
FIG. 10A-10C. Spt4 is specifically required for expression of genes with a long stretch of CAG repeats, related to FIG. 2A-2F (FIG. 10A) Colony color phenotypes of cells expressing 99Q-Ade2 or 29Q-Ade2. In these reporter proteins, distinct from 97Q-Ade2 and 25Q-Ade2, successive glutamine residues are encoded by CAG repeats only.
Figure 10B:
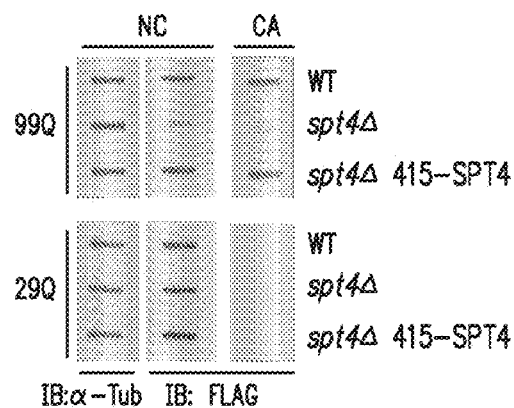
Figure 10C:
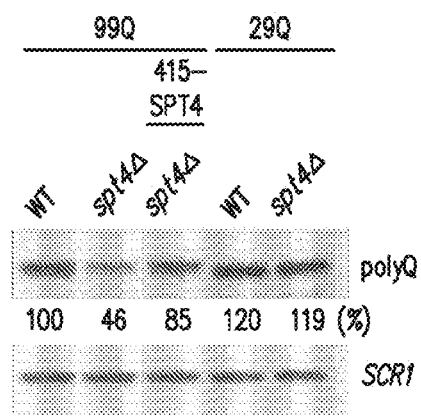
Figure 12A:
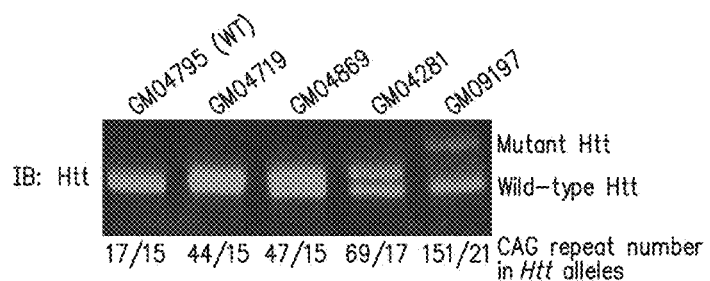
FIG. 12A-12C. A long stretch of CAG repeats is associated with reduced Htt expression in HD patient-derived fibroblasts, related to FIG. 6A-6D (FIG. 12A) Htt protein expression from wild-type and mutant alleles was examined by immunoblotting of indicated cells, which were obtained from the Coriell Institute. GM04795 is a normal fibroblast cell line.
Figure 12B:
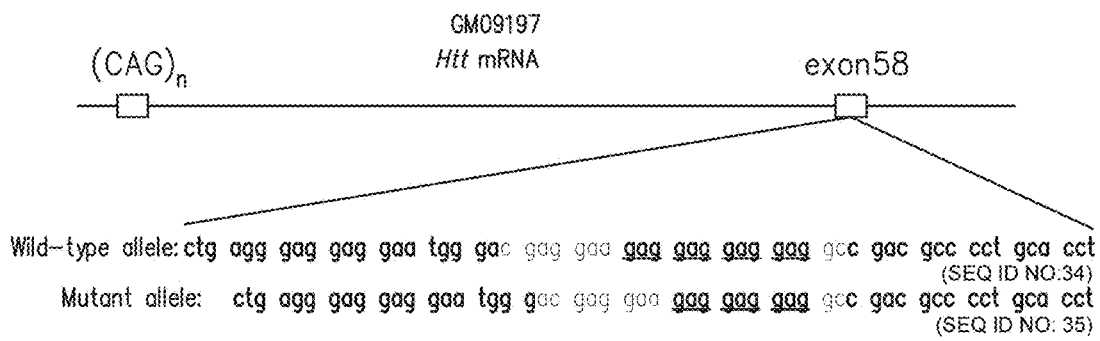
Figure 12C:
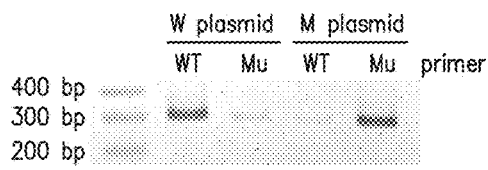
Figure 12C:
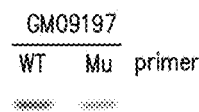

Unlike yeast cell mutations that result in an overall reduction in mRNA synthesis by RNA polymerase II (Rondon, A. G., Garcia-Rubio, M., Gonzalez-Barrera, S., and Aguilera, A. (2003). Molecular evidence for a positive role of Spt4 in transcription elongation. EMBO J 22, 612-620), spt4 mutant cells showed little effect on the production of mRNA encoding short polyQ protein (i.e., 25Q-Ade2) (FIG. 2C), or on the color of yeast colonies carrying this mutant gene (FIGS. 2B and 2A), showing that Spt4 is not necessary for elongation of transcripts containing only a short stretch of CAG repeats. That Spt4 is required specifically for the expression of genes containing a long stretch of CAG repeats was confirmed directly by using reporter gene constructs that harbor long vs. short CAG stretches (99Q-ADE2 and 29Q-ADE2, respectively, FIG. 10). The yeast cell requirement for Spt4 to specifically elongate transcripts having long stretches of tri-nucleotide repeats is not restricted to Ade2-encoding transcripts: deletion of SPT4 also resulted in delayed and reduced aggregation of GFP protein from a construct containing 65 repeats of CAG (i.e., 65Q-eGFP) (FIG. 2D).

Like Spt4, the THO complex, which is formed by interaction of the Hpr1, Mft1, Tho2, and Thp2 proteins, promotes transcript elongation by RNA polymerase II. Whereas the THO complex is required for transcription of yeast genes that include multiple tandemly repeated sequences (Voynov, V., Verstrepen, K. J., Jansen, A., Runner, V. M., Buratowski, S., and Fink, G. R. (2006). Genes with internal repeats require the THO complex for transcription. Proc Natl Acad Sci USA 103, 14423-14428), THO and Spt4 affect RNA polymerase II processivity by different mechanisms (Mason, P. B., and Struhl, K. (2005). Distinction and relationship between elongation rate and processivity of RNA polymerase II in vivo. Mol Cell 17, 831-840). In contrast to spt4Δ cells, we found that cells defective in the THO complex (i.e., thp2Δ☐ showed severely impaired production of Ade2 protein containing 25Q repeats as well as of the Ade2 variant containing 97Q repeats (FIG. 2E), and failed to show complementation of ade2 deficiency by either of the adventitiously expressed constructs (FIG. 2F). These results indicate that unlike Spt4, THO does not differentiate between transcripts containing short vs. long stretches of the CAG tri-nucleotide repeat and that deficiency of THO results in a general defect in polyQ protein synthesis.

Mutation in SPT4 has been reported to especially affect transcription of genes of high GC content (Rondon et al., 2003, supra) and we hypothesized that long stretches of CAG repeats may create a local barrier for RNA polymerase II that is overcome by the actions of the transcription elongation factor encoded by this gene. Using chromatin immunoprecipitation assays to assess RNA polymerase II occupancy on different segments of DNA templates, we found that the amount of enzyme bound to transcript sequences downstream of a stretch of 99 CAG repeats was reduced by spt4 deficiency, whereas occupancy of DNA segments upstream or downstream from a 29 CAG repeat segment was similar in SPT4$^+$ and spt4Δ cells (FIG. 3). We conclude from this finding that Spt4 is dispensable for passage of the transcriptional machinery through a region containing a short stretch of CAG repeats, but is required for the polymerase to proceed through a long expansion of the CAG repeat sequence.

Figure 4A:
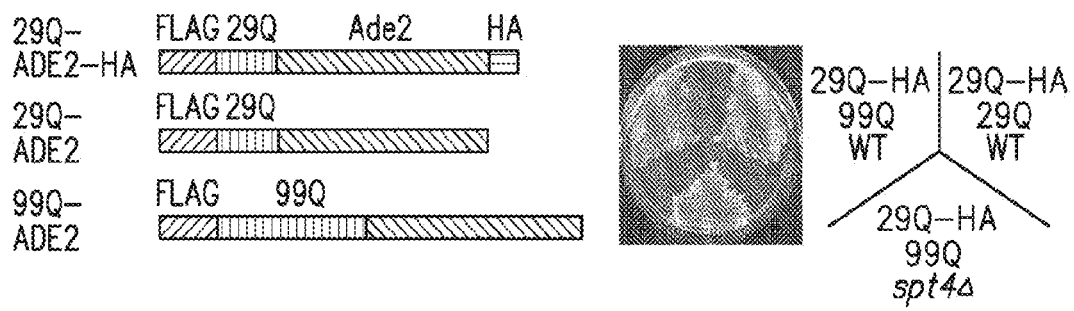
FIG. 4A-4C. Co-aggregation of short polyQ-containing proteins is attenuated by spt4 deficiency (FIG. 4A) Colony color phenotypes of cells expressing indicated constructs. 29Q-ADE2-HA along with plasmid constructs as described in FIG. 10A-10C were co-introduced into cells.
Figure 4B:
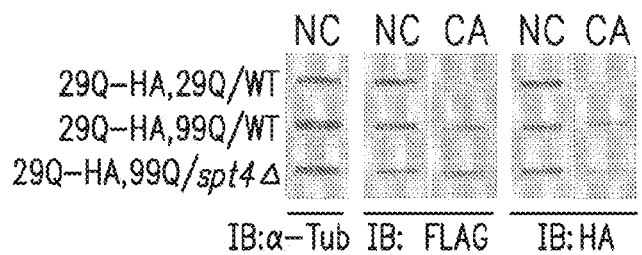
Figure 4C:
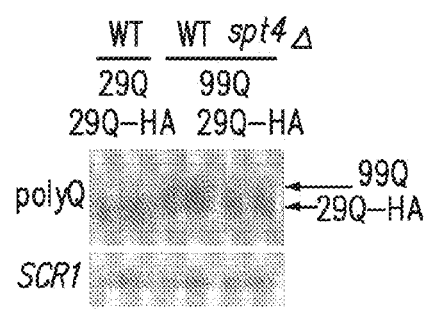

C. Mutation of SPT4 Enhances the Function of Normal Protein Containing Short polyQ Stretches by Diminishing their Co-aggregation with Concomitantly Present Long polyQ Protein Interaction between proteins containing an expanded polyQ repeat with proteins containing a short non-pathogenic stretch of polyQ results in co-aggregation of short and long polyQ proteins in both mammalian cells and yeast (Duennwald, M. L., Jagadish, S., Giorgini, F., Muchowski, P. J., and Lindquist, S. (2006). A network of protein interactions determines polyglutamine toxicity. Proc Natl Acad Sci USA 103, 11051-11056; Kazantsev, A., Preisinger, E., Dranovsky, A., Goldgaber, D., and Housman, D. (1999). Insoluble detergent-resistant aggregates form between pathological and nonpathological lengths of polyglutamine in mammalian cells. Proc Natl Acad Sci USA 96, 11404-11409). To learn whether reduction of long-polyQ-protein aggregation by spt4 deficiency can affect concomitantly present normal-polyQ protein, we co-expressed 99Q-Ade2 together with 29Q-Ade2 tagged at the C-terminal end with hemaglutinin (29Q-Ade2-HA) and examined the effects of SPT4 mutation on both Ade2 function on the colorimetric assay and on co-aggregation of the proteins. As described above, in wild-type W303-1A cells, expression of either 29Q-Ade2-HA or 29Q-Ade2 or both resulted in a white colony color. However, a red colony color was observed when 29Q-Ade2-HA was co-expressed with 99Q-Ade2 (FIG. 4A), reminiscent of cells expressing 99Q-Ade2 alone (FIG. 10)— indicating that 99Q-Ade2 is phenotypically dominant over 29Q-Ade2-HA. In agreement with this conclusion, 29Q-Ade2-HA, which normally is soluble in the absence of the long polyQ protein, was present in cellular aggregates formed in cells expressing 99Q-Ade2 (FIG. 4B). The effect of 99Q-Ade2 expression on concomitantly present 29Q-Ade2-HA was greatly reduced by spt4 deficiency, as revealed by the change of colony color from red to white (FIG. 4A). In addition, the overall extent of 29Q-Ade2-HA aggregation was substantially decreased in spt4 mutant cells (FIG. 4B) even though the amount of corresponding protein and mRNA was not altered by the lack of Spt4 (FIGS. 4B and 4C). These results demonstrate that selective regulation of the production of protein encoded by genes containing long stretches of CAG tri-nucleotide repeats by Spt4 additionally can indirectly affect the aggregation and functioning of protein encoded by a co-existing allele containing short CAG repeats.

D. Supt4h, a Mammalian Ortholog of Spt4, Affects Abundance and Aggregation of polyQ Proteins in Neurons SPT4 is highly conserved between yeast and mammalian cells, and yeast spt4 defects can be functionally complemented by the mammalian cell ortholog Supt4h (Hartzog, G. A., Basrai, M. A., Ricupero-Hovasse, S. L., Hieter, P., and Winston, F. (1996). Identification and analysis of a functional human homolog of the SPT4 gene of *Saccharomyces cerevisiae*. Mol Cell Biol 16, 2848-2856). Using siRNA to reduce expression of Supt4h in the murine striatal cell line ST14A (Ehrlich, M. E., Conti, L., Toselli, M., Taglietti, L., Fiorillo, E., Taglietti, V., Ivkovic, S., Guinea, B., Tranberg, A., Sipione, S., et al. (2001). ST14A cells have properties of a medium-size spiny neuron. Exp Neurol 167, 215-226), we found that in a population of cells showing approximately 60% down-regulation of Supt4h, the number of cells showing aggregated eGFP-positive foci was decreased by approximately one half (FIGS. 5A and 5B), that the cellular abundance of a GFP protein containing an 81 amino acid stretch of poly Q (i.e., 81Q-eGFP) was reduced, and that overall aggregation of the eGFP protein was decreased by 65% (FIG. 5C), as compared to a cell population transfected with a negative control siRNA. By contrast, expression of 7Q-eGFP was affected only minimally by Supt4h knockdown (FIGS. 5A, 5B, and 5C), suggesting that other transcription elongation components can largely compensate for the absence of Supt4h to enable transcription of short polyQ-encoding messages. As the aggregation of proteins containing expanded polyQ stretches is toxic to neuronal cells (Li, H., Li, S. H., Johnston, H., Shelbourne, P. F., and Li, X. J. (2000). Amino-terminal fragments of mutant huntingtin show selective accumulation in striatal neurons and synaptic toxicity. Nat Genet 25, 385-389; Varma, H., Voisine, C., DeMarco, C. T., Cattaneo, E., Lo, D. C., Hart, A. C., and Stockwell, B. R. (2007). Selective inhibitors of death in mutant huntingtin cells. Nat Chem Biol 3, 99-100), we asked whether cell survival was enhanced by attenuating polyQ aggregation through Supt4h knockdown. ST14A cells were transfected with polyQ-eGFP constructs in the presence or absence of Supt4h siRNA. As seen in FIG. 5D, the reduced viability of STI4A cells that adventitiously express the 81Q-eGFP protein was reversed by siRNA directed against Supt4h and that such siRNA had no detectable effect on the viability of cells producing the 7Q-eGFP protein.

To learn the effects of Supt4h knockdown specifically on the production of huntingtin (Htt), striatal neurons derived from homozygous Hdh$^{Q7/Q7}$ and Hdh$^{Q111/Q111}$ knock-in mice (Trettel, F., Rigamonti, D., Hilditch-Maguire, P., Wheeler, V. C., Sharp, A. H., Persichetti, F., Cattaneo, E., and MacDonald, M. E. (2000). Dominant phenotypes produced by the HD mutation in STHdh(Q111) striatal cells.

Figure 6A:
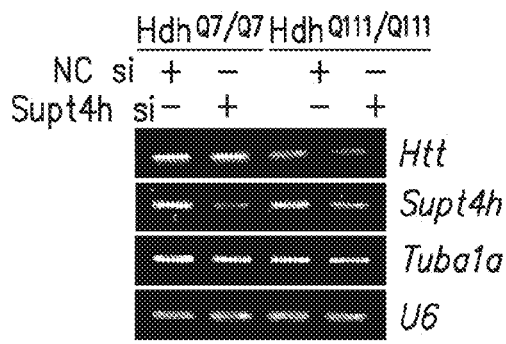
FIG. 6A-6D. Mutant Htt expression is selectively inhibited by Supt4h down-regulation (FIG. 6A) Htt mRNA abundance was examined by RT-PCR following Supt4h siRNA knockdown in striatal cells possessing homozygous wild-type ($Hdh^{Q7/Q7}$) or mutant huntingtin alleles ($Hdh^{Q111/Q111}$). U6, which is transcribed by RNA polymerase III, serves as loading control. Tuba1a was included to determine the effect of Supt4h on pol II-dependent transcription of housekeeping genes. See also FIG. 12A-12C.
Figure 6B:
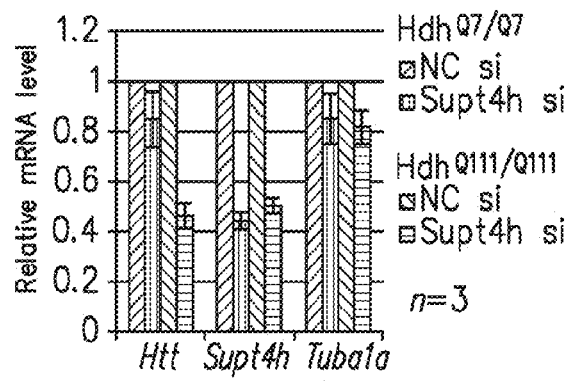
Figure 6C:
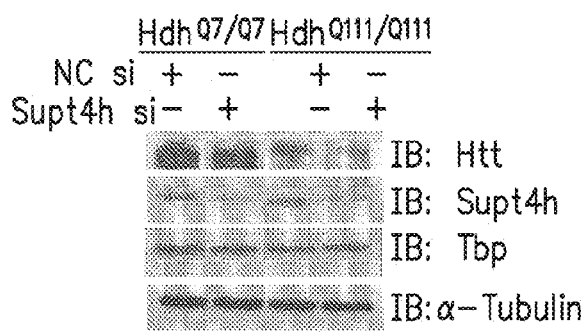
Figure 6D:
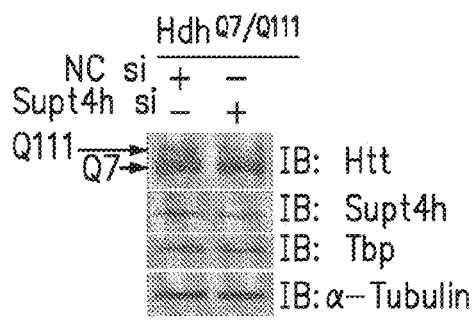

Hum Mol Genet 9, 2799-2809) were analyzed following Supt4h knockdown by siRNA. Both RT-PCR and quantitative real-time RT-PCR showed $Htt^{Q7}$ mRNA abundance was only slightly diminished in cells treated with siRNA directed against Supt4h, as was the abundance of α-Tubulin mRNA in the elongation-factor-deficient cells. However, the abundance of mutant $Htt^{Q111}$ mRNA was substantially reduced (FIGS. 6A and 6B) in cells having a similar reduction of Supt4h mRNA. Concurrently with the observed reduction of $Htt^{Q111}$ mRNA, $Htt^{Q111}$ protein was decreased; however, production of $Htt^{Q7}$ and Tbp, which contain only short stretches of glutamine, was not detectably affected by Supt4h down-regulation (FIG. 6C). Importantly, Supt4h knockdown in heterozygous $Hdh^{Q7/Q111}$ cells showed that $Htt^{Q111}$ and Supt4h protein were concomitantly reduced in the presence of Supt4h siRNA, but that the same extent of Supt4h knockdown had little effect on $Htt^{Q7}$ expression (FIG. 6D). These findings show that Supt4h is differentially required for expression of the mutant Htt allele in mouse striatal neurons.

III. Discussion

Our investigations, which reveal a specific role for transcription elongation factors Spt4 and Supt4h in the expression of genes containing long tri-nucleotide repeats, offer an approach to the reduction of aggregating proteins affected by long-tri-nucleotide-repeat transcripts while still allowing virtually normal synthesis of protein encoded by other mRNAs. Whereas it has been suggested that proteins containing extended polyQ tracts are inherently prone to misfolding (Krobitsch and Lindquist, 2000, supra; Ordway et al., 1997, supra), our results indicate that long polyQ proteins can fold properly enough to exhibit enzymatic activity if their production is simply decreased to a level low enough to diminish their aggregation. In yeast, we have shown that synthesis of proteins containing long polyQ repeats can be reduced by spt4 deficiency to a level that restores protein functionality. Under such conditions, non-aggregating polyQ protein can complement ade2 deficiency in the assay we used to identify loci that affect the function of protein containing extended polyQ repeats. We have further demonstrated that the effects of Spt4 (Supt4h) on yeast and mammalian cells are allele specific: deficiency of Spt4 specifically reduces the ability of RNA polymerase II to proceed through extended stretches of CAG repeats and reduces the abundance of proteins that these transcripts encode without significantly affecting transcripts from a co-existing non-mutant Htt allele. As Htt is required embryonically and for normal neurological function in adults (Dragatsis, I., Levine, M. S., and Zeitlin, S. (2000). Inactivation of Hdh in the brain and testis results in progressive neurodegeneration and sterility in mice. Nat Genet 26, 300-306; Nasir, J., Floresco, S. B., O'Kusky, J. R., Diewert, V. M., Richman, J. M., Zeisler, J., Borowski, A., Marth, J. D., Phillips, A. G., and Hayden, M. R. (1995). Targeted disruption of the Huntington's disease gene results in embryonic lethality and behavioral and morphological changes in heterozygotes. Cell 81, 811-823), the ability to differentially reduce the neurotoxicity of mutant Htt protein will benefit HD patients and small molecule inhibitors of Supt4h are a viable approach to the treatment of Huntington's disease.

Scherzinger et al. (1999, supra) found that the formation of amyloid-like huntingtin protein aggregates in vitro did not occur until the monomer concentration exceeded a critical level. Our results establish that the concentration of proteins containing long polyQ stretches is also a critical determinant of the ability of these proteins to undergo pathological aggregation in vivo and further demonstrate the value of decreasing long polyQ protein to a concentration where aggregation is diminished and functionality is restored. Importantly, we also found that the previously observed (Duennwald et al, 2006, supra) co-aggregation of a normal short polyQ protein with an expanded polyQ protein that has been produced by a second allele in the same cell was sharply reduced by a decrease in the abundance of the long polyQ variant protein. Thus, reduction in mutant Htt protein abundance by interference with Supt4h function may not only decrease the direct toxic effects of mutant protein aggregation, but may also allow increased functionality of the coexisting wild-type protein.

Human Supt4h normally forms a complex with Supt5h as does its yeast ortholog to regulate transcription elongation (Guo, M., Xu, F., Yamada, J., Egelhofer, T., Gao, Y., Hartzog, G. A., Teng, M., and Niu, L. (2008). Core structure of the yeast spt4-spt5 complex: a conserved module for regulation of transcription elongation. Structure 16, 1649-1658; Hatzog et al., 1998, supra; Wada, T., Takagi, T., Yamaguchi, Y., Ferdous, A., Imai, T., Hirose, S., Sugimoto, S., Yano, K., Hartzog, G. A., Winston, F., et al. (1998). DSIF, a novel transcription elongation factor that regulates RNA polymerase II processivity, is composed of human Spt4 and Spt5 homologs. Genes Dev 12, 343-356; Wenzel, S., Martins, B. M., Rosch, P., and Wohrl, B. M. (2009). Crystal structure of the human transcription elongation factor DSIF hSpt4 subunit in complex with the hSpt5 dimerization interface. Biochem J 425, 373-380). This complex is bound to the coiled coil domain of RNA polymerase II and encircles the DNA to promote processivity (Klein, B. J., Bose, D., Baker, K. J., Yusoff, Z. M., Zhang, X., and Murakami, K. S. (2011). RNA polymerase and transcription elongation factor Spt4/5 complex structure. Proc Natl Acad Sci USA 108, 546-550; Martinez-Rucobo, F. W., Sainsbury, S., Cheung, A. C., and Cramer, P. (2011). Architecture of the RNA polymerase-Spt4/5 complex and basis of universal transcription processivity. EMBO J 30, 1302-1310). Notably, the effects of spt4Δ on polyQ gene expression can be recapitulated by a unique spt5 mutant that cannot interact with its binding partner Spt4 (FIG. 11). Thus, an intact Spt4/5 complex for transcription elongation is critical for production of mRNAs encoding expanded polyQ. As SPT4 is not an essential gene (Malone, E. A., Fassler, J. S., and Winston, F. (1993). Molecular and genetic characterization of SPT4, a gene important for transcription initiation in *Saccharomyces cerevisiae*. Mol Gen Genet 237, 449-459) and the protein it encodes does not directly contact RNA polymerase, as revealed by crystal structure analyses, Spt4 is likely to function as an "upstream DNA holder" that stabilizes polymerase/template complexes by binding to DNA externally to the transcription bubble (Klein et al., 2011, supra; Martinez-Rucobo et al., 2011, supra). A Zinc-finger domain in Spt4 mediates this protein-DNA interaction, and point mutations that disable this domain have the same effect on long polyQ gene expression as deletion of SPT4 (data not shown)—suggesting that the complex stabilizing actions of Spt4 are important for RNA polymerase II transcription through template regions containing multiple CAG repeats.

Figure 7:
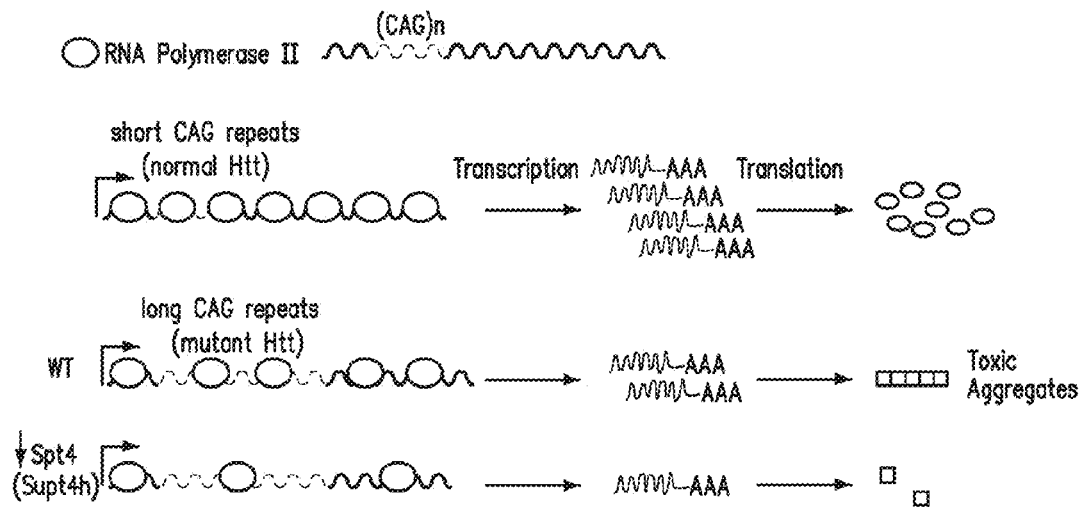
FIG. 7. Model depicting the effect and consequence of Spt4 (Supt4h) down-regulation on expression of CAG-containing genes. When RNA polymerase II moves along a DNA template containing a short CAG repeat (indicated in red), transcript elongation is not regulated by Spt4. However, transcription elongation becomes less efficient and requires Spt4 when a long CAG stretch is present in the gene. In cells lacking normal Spt4 function, only genes containing extended stretches of CAG repeats and encoding expanded polyQ proteins are affected. Proteins containing expanded polyQ repeat (squares) aggregate (rectangle) in a concentration-dependent manner.

During these investigations, we discovered that a long stretch of CAG repeats reduces transcript abundance in both yeast and mammalian cells. Specifically, even in the presence of Supt4h, the transcripts of mutant Htt allele were produced much less efficiently than wild-type transcripts in neurons from knock-in mice as well as in fibroblasts from HD patients (FIG. 6A and FIG. 12). In vitro, expanded CAG repeats have been shown to form stem-loops or higher order DNA structures (Lenzmeier, B. A., and Freudenreich, C. H. (2003). Trinucleotide repeat instability: a hairpin curve at the crossroads of replication, recombination, and repair. Cytogenet Genome Res 100, 7-24), causing RNA polymerase II to pause temporarily and dissociate from the template. Our data show that the transcriptional block posed by such a structural barrier is affected by the length of the repeat sequence. Our results show that in the absence of Spt4 function, dissociation of RNA polymerase from the template in extended CAG repeat regions is increased, resulting in 1) reduction of template-bound polymerase distal to the extended repeat, 2) an overall decrease in transcript abundance, 3) reduced production of long polyQ protein, and 4) decreased aggregation of this protein. This mechanistic model, which is shown in FIG. 7, provides a molecular basis for HD countermeasures that target the functions of Supt4h.

Recent work has shown that allele-specific reduction in mutant Htt abundance can also be accomplished using RNAi-based approaches (Hu, J., Matsui, M., Gagnon, K. T., Schwartz, J. C., Gabillet, S., Arar, K., Wu, J., Bezprozvanny, I., and Corey, D. R. (2009). Allele-specific silencing of mutant huntingtin and ataxin-3 genes by targeting expanded CAG repeats in mRNAs. Nat Biotechnol 27, 478-484; Pfister, E. L., Kennington, L., Straubhaar, J., Wagh, S., Liu, W., DiFiglia, M., Landwehrmeyer, B., Vonsattel, J. P., Zamore, P. D., and Aronin, N. (2009). Five siRNAs targeting three SNPs may provide therapy for three-quarters of Huntington's disease patients. Curr Biol 19, 774-778; van Bilsen, P. H., Jaspers, L., Lombardi, M. S., Odekerken, J. C., Burright, E. N., and Kaemmerer, W. F. (2008). Identification and allele-specific silencing of the mutant huntingtin allele in Huntington's disease patient-derived fibroblasts. Hum Gene Ther 19, 710-719; Zhang, Y., Engelman, J., and Friedlander, R. M. (2009). Allele-specific silencing of mutant Huntington's disease gene. J Neurochem 108, 82-90), or by targeting the mutant protein for degradation by an engineered fusion protein comprising a polyglutamine binding peptide 1 (QBP1) and two different heat shock cognate protein 70 (HSC70)-binding motifs (Bauer, P. O., Goswami, A., Wong, H. K., Okuno, M., Kurosawa, M., Yamada, M., Miyazaki, H., Matsumoto, G., Kino, Y., Nagai, Y., et al. (2010). Harnessing chaperone-mediated autophagy for the selective degradation of mutant huntingtin protein. Nat Biotechnol 28, 256-263). However, recent evidence suggests that siRNAs containing tri-nucleotide repeats may in fact contribute to the toxic effects of extended CAG repeats of mRNAs (Yu, Z., Teng, X., and Bonini, N. M. (2011). Triplet repeat-derived siRNAs enhance RNA-mediated toxicity in a *Drosophila* model for myotonic dystrophy. PLoS Genet 7, e1001340). Additionally, the therapeutic potential of siRNA and protein-fusion based approaches seems likely to be limited by the inability of these agents to pass through the blood-brain barrier (BBB) (Lichota, J., Skjorringe, T., Thomsen, L. B., and Moos, T. (2010). Macromolecular drug transport into the brain using targeted therapy. J Neurochem 113, 1-13). Small molecule inhibitors of Supt4h that are accessible to the brain will overcome such limitations.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of reducing the deleterious activity in a cell of a target gene comprising a mutant extended trinucleotide repeat domain, the method comprising:
   providing in the cell an effective amount of an SPT4 modulatory agent that reduces the deleterious impact of the target gene in the cell.

2. The method according to claim 1, wherein the agent modulates the activity of a protein encoded by the gene comprising mutant extended trinucleotide repeat domain.

3. The method according to claim 2, wherein deleterious impact of the gene is toxicity of the protein and the agent reduces the toxicity of the protein in the cell.

4. The method according to claim 2, wherein the deleterious impact of the gene is loss of function of the protein and the agent enhances functionality of the protein in the cell.

5. The method according to claim 2, wherein the agent modulates deleterious activity of the protein encoded by the gene following expression.

6. The method according to claim 2, wherein the agent modulates expression of the protein from the gene.

7. The method according to claim 6, wherein the agent reduces transcription of the gene to enhance functionality of the protein in the cell.

8. The method according to claim 6, wherein the agent reduces transcription of the gene to reduce toxicity of the protein in the cell.

9. The method according to claim 1, wherein the agent inhibits binding of the SPT4 protein to a second protein.

10. The method according to claim 1, wherein the agent inhibits expression of the SPT4 protein.

11. The method according to claim 1, wherein the mutant trinucleotide repeat domain is present in a coding region of the gene.

12. The method according to claim 1, wherein the mutant trinucleotide repeat domain is present in the non-coding region of the gene.

13. The method according to claim 1, wherein the cell is in vivo.

14. A method of modifying progression in a subject of a disease arising from a gene containing a mutant extended trinucleotide repeat domain, the method comprising:
   administering to the subject an effective amount of an SPT4 modulatory agent that reduces the deleterious activity of the gene to modify progression of the disease in the subject.

15. The method according to claim 14, wherein the mutant extended trinucleotide repeat domain is a CAG repeat domain.

16. The method according to claim 15, wherein the mutant extended trinucleotide repeat domain comprises 35 or more CAG repeats.

17. The method according to claim 14, wherein the mutant extended trinucleotide repeat domain is a CTG repeat domain.

18. The method according to claim 14, wherein the agent inhibits binding of the SPT4 protein to a second protein.

19. The method according to claim 14, wherein the agent inhibits expression of the SPT4 protein.

20. The method according to claim 14, wherein the gene is an HTT gene.

* * * * *

SEQUENCE LISTING

```
<160> NUMBER OF SEQ ID NOS: 35

<210> SEQ ID NO 1
<211> LENGTH: 18
<212> TYPE: DNA
<213> ORGANISM: Artificial Sequence
<220> FEATURE:
<223> OTHER INFORMATION: Synthetic Nucleic Acid Sequence

<400> SEQUENCE: 1
cagcagcagc agcagcag                                                 18

<210> SEQ ID NO 2
<211> LENGTH: 18
<212> TYPE: DNA
<213> ORGANISM: Artificial Sequence
<220> FEATURE:
<223> OTHER INFORMATION: Synthetic Nucleic Acid Sequence
```

```
<400> SEQUENCE: 2
ctgctgctgc tgctgctg                                              18

<210> SEQ ID NO 3
<211> LENGTH: 21
<212> TYPE: RNA
<213> ORGANISM: Artificial Sequence
<220> FEATURE:
<223> OTHER INFORMATION: Synthetic Nucleic Acid Sequence

<400> SEQUENCE: 3
uggccuacaa aucgagagau u                                          21

<210> SEQ ID NO 4
<211> LENGTH: 21
<212> TYPE: RNA
<213> ORGANISM: Artificial Sequence
<220> FEATURE:
<223> OTHER INFORMATION: Synthetic Nucleic Acid Sequence

<400> SEQUENCE: 4
ucucucgauu uguaggccau u                                          21

<210> SEQ ID NO 5
<211> LENGTH: 21
<212> TYPE: DNA
<213> ORGANISM: Artificial Sequence
<220> FEATURE:
<223> OTHER INFORMATION: Synthetic Nucleic Acid Sequence; Combined
      DNA/RNA molecule.

<400> SEQUENCE: 5
uucuccgaac gugucacgut t                                          21

<210> SEQ ID NO 6
<211> LENGTH: 21
<212> TYPE: DNA
<213> ORGANISM: Artificial Sequence
<220> FEATURE:
<223> OTHER INFORMATION: Synthetic Nucleic Acid Sequence; Combined
      DNA/RNA molecule.

<400> SEQUENCE: 6
acgugacacg uucggagaat t                                          21

<210> SEQ ID NO 7
<211> LENGTH: 18
<212> TYPE: DNA
<213> ORGANISM: Artificial Sequence
<220> FEATURE:
<223> OTHER INFORMATION: Synthetic Nucleic Acid Sequence

<400> SEQUENCE: 7
cagcagcaac agcaacaa                                              18

<210> SEQ ID NO 8
<211> LENGTH: 25
<212> TYPE: DNA
<213> ORGANISM: Artificial Sequence
<220> FEATURE:
<223> OTHER INFORMATION: Synthetic Nucleic Acid Sequence

<400> SEQUENCE: 8
taagttgggt aacgccaggg ttttc                                      25
```

<210> SEQ ID NO 9
<211> LENGTH: 25
<212> TYPE: DNA
<213> ORGANISM: Artificial Sequence
<220> FEATURE:
<223> OTHER INFORMATION: Synthetic Nucleic Acid Sequence

<400> SEQUENCE: 9
ttccatgttg ccactcgctt taatg						25

<210> SEQ ID NO 10
<211> LENGTH: 28
<212> TYPE: DNA
<213> ORGANISM: Artificial Sequence
<220> FEATURE:
<223> OTHER INFORMATION: Synthetic Nucleic Acid Sequence

<400> SEQUENCE: 10
cccccttaac gtgagttttc gttccact						28

<210> SEQ ID NO 11
<211> LENGTH: 20
<212> TYPE: DNA
<213> ORGANISM: Artificial Sequence
<220> FEATURE:
<223> OTHER INFORMATION: Synthetic Nucleic Acid Sequence

<400> SEQUENCE: 11
actacaagga cgacgatgac						20

<210> SEQ ID NO 12
<211> LENGTH: 22
<212> TYPE: DNA
<213> ORGANISM: Artificial Sequence
<220> FEATURE:
<223> OTHER INFORMATION: Synthetic Nucleic Acid Sequence

<400> SEQUENCE: 12
cctcctaata taccaactgt tc						22

<210> SEQ ID NO 13
<211> LENGTH: 21
<212> TYPE: DNA
<213> ORGANISM: Artificial Sequence
<220> FEATURE:
<223> OTHER INFORMATION: Synthetic Nucleic Acid Sequence

<400> SEQUENCE: 13
ggctgtaatg gctttctggt g						21

<210> SEQ ID NO 14
<211> LENGTH: 21
<212> TYPE: DNA
<213> ORGANISM: Artificial Sequence
<220> FEATURE:
<223> OTHER INFORMATION: Synthetic Nucleic Acid Sequence

<400> SEQUENCE: 14
accagacaga gagacggatt c						21

<210> SEQ ID NO 15
<211> LENGTH: 23
<212> TYPE: DNA
<213> ORGANISM: Artificial Sequence
<220> FEATURE:
<223> OTHER INFORMATION: Synthetic Nucleic Acid Sequence

```
<400> SEQUENCE: 15
gatggcagta gtggaagata ttc                                          23

<210> SEQ ID NO 16
<211> LENGTH: 22
<212> TYPE: DNA
<213> ORGANISM: Artificial Sequence
<220> FEATURE:
<223> OTHER INFORMATION: Synthetic Nucleic Acid Sequence

<400> SEQUENCE: 16
caatggacca gaactacctg tg                                           22

<210> SEQ ID NO 17
<211> LENGTH: 26
<212> TYPE: DNA
<213> ORGANISM: Artificial Sequence
<220> FEATURE:
<223> OTHER INFORMATION: Synthetic Nucleic Acid Sequence

<400> SEQUENCE: 17
ttttcggttt gtattacttc ttattc                                       26

<210> SEQ ID NO 18
<211> LENGTH: 21
<212> TYPE: DNA
<213> ORGANISM: Artificial Sequence
<220> FEATURE:
<223> OTHER INFORMATION: Synthetic Nucleic Acid Sequence

<400> SEQUENCE: 18
gaaggccttc atcagctttt c                                            21

<210> SEQ ID NO 19
<211> LENGTH: 22
<212> TYPE: DNA
<213> ORGANISM: Artificial Sequence
<220> FEATURE:
<223> OTHER INFORMATION: Synthetic Nucleic Acid Sequence

<400> SEQUENCE: 19
tccggaagct ttggaagtac tg                                           22

<210> SEQ ID NO 20
<211> LENGTH: 22
<212> TYPE: DNA
<213> ORGANISM: Artificial Sequence
<220> FEATURE:
<223> OTHER INFORMATION: Synthetic Nucleic Acid Sequence

<400> SEQUENCE: 20
taagttgaac ggagtccgga ac                                           22

<210> SEQ ID NO 21
<211> LENGTH: 23
<212> TYPE: DNA
<213> ORGANISM: Artificial Sequence
<220> FEATURE:
<223> OTHER INFORMATION: Synthetic Nucleic Acid Sequence

<400> SEQUENCE: 21
ggttcctcag tgtacttata tgg                                          23

<210> SEQ ID NO 22
<211> LENGTH: 22
```

```
<212> TYPE: DNA
<213> ORGANISM: Artificial Sequence
<220> FEATURE:
<223> OTHER INFORMATION: Synthetic Nucleic Acid Sequence

<400> SEQUENCE: 22
tttaaaaccg cacatgcggc ag                                        22

<210> SEQ ID NO 23
<211> LENGTH: 21
<212> TYPE: DNA
<213> ORGANISM: Artificial Sequence
<220> FEATURE:
<223> OTHER INFORMATION: Synthetic Nucleic Acid Sequence

<400> SEQUENCE: 23
ccattggcaa ggagatcatt g                                         21

<210> SEQ ID NO 24
<211> LENGTH: 21
<212> TYPE: DNA
<213> ORGANISM: Artificial Sequence
<220> FEATURE:
<223> OTHER INFORMATION: Synthetic Nucleic Acid Sequence

<400> SEQUENCE: 24
atggcctcat tgtctaccat g                                         21

<210> SEQ ID NO 25
<211> LENGTH: 21
<212> TYPE: DNA
<213> ORGANISM: Artificial Sequence
<220> FEATURE:
<223> OTHER INFORMATION: Synthetic Nucleic Acid Sequence

<400> SEQUENCE: 25
ctttccgtaa tccacagaga g                                         21

<210> SEQ ID NO 26
<211> LENGTH: 21
<212> TYPE: DNA
<213> ORGANISM: Artificial Sequence
<220> FEATURE:
<223> OTHER INFORMATION: Synthetic Nucleic Acid Sequence

<400> SEQUENCE: 26
tcattgcgat gatgagtcca g                                         21

<210> SEQ ID NO 27
<211> LENGTH: 21
<212> TYPE: DNA
<213> ORGANISM: Artificial Sequence
<220> FEATURE:
<223> OTHER INFORMATION: Synthetic Nucleic Acid Sequence

<400> SEQUENCE: 27
tttcgtggag tctgctgatt c                                         21

<210> SEQ ID NO 28
<211> LENGTH: 21
<212> TYPE: DNA
<213> ORGANISM: Artificial Sequence
<220> FEATURE:
<223> OTHER INFORMATION: Synthetic Nucleic Acid Sequence

<400> SEQUENCE: 28
```

```
gctgtgtctc tggatttgta g                                              21
```

<210> SEQ ID NO 29
<211> LENGTH: 21
<212> TYPE: DNA
<213> ORGANISM: Artificial Sequence
<220> FEATURE:
<223> OTHER INFORMATION: Synthetic Nucleic Acid Sequence

<400> SEQUENCE: 29

```
tcctgatcag tgaagtggtt c                                              21
```

<210> SEQ ID NO 30
<211> LENGTH: 21
<212> TYPE: DNA
<213> ORGANISM: Artificial Sequence
<220> FEATURE:
<223> OTHER INFORMATION: Synthetic Nucleic Acid Sequence

<400> SEQUENCE: 30

```
gtcacactcc aacacataga g                                              21
```

<210> SEQ ID NO 31
<211> LENGTH: 22
<212> TYPE: DNA
<213> ORGANISM: Artificial Sequence
<220> FEATURE:
<223> OTHER INFORMATION: Synthetic Nucleic Acid Sequence

<400> SEQUENCE: 31

```
aaaaatatgg aacgcttcac ga                                             22
```

<210> SEQ ID NO 32
<211> LENGTH: 20
<212> TYPE: DNA
<213> ORGANISM: Artificial Sequence
<220> FEATURE:
<223> OTHER INFORMATION: Synthetic Nucleic Acid Sequence

<400> SEQUENCE: 32

```
ctcgcttcgg cagcacatat                                                20
```

<210> SEQ ID NO 33
<211> LENGTH: 22
<212> TYPE: DNA
<213> ORGANISM: Artificial Sequence
<220> FEATURE:
<223> OTHER INFORMATION: Synthetic Nucleic Acid Sequence

<400> SEQUENCE: 33

```
tatggaacgc ttcacgaatt tg                                             22
```

<210> SEQ ID NO 34
<211> LENGTH: 57
<212> TYPE: DNA
<213> ORGANISM: Artificial Sequence
<220> FEATURE:
<223> OTHER INFORMATION: Synthetic Nucleic Acid Sequence

<400> SEQUENCE: 34

```
ctgagggagg aggaatggga cgaggaagag gaggaggagg ccgacgcccc tgcacct       57
```

<210> SEQ ID NO 35
<211> LENGTH: 54
<212> TYPE: DNA
<213> ORGANISM: Artificial Sequence

```
<220> FEATURE:
<223> OTHER INFORMATION: Synthetic Nucleic Acid Sequence

<400> SEQUENCE: 35
ctgagggagg aggaatggga cgaggaagag gaggaggccg acgcccctgc acct          54
```